(12) United States Patent
Barker et al.

(10) Patent No.: US 9,393,041 B2
(45) Date of Patent: Jul. 19, 2016

(54) EXPANDABLE MEDICAL ACCESS SHEATH

(75) Inventors: Peter Barker, Lake Forest, CA (US);
Jay Lenker, Laguna Beach, CA (US);
Edward Nance, Corona, CA (US)

(73) Assignee: Onset Medical Corporation, Irvine, CA (US)

( * ) Notice: Subject to any disclaimer, the term of this patent is extended or adjusted under 35 U.S.C. 154(b) by 2168 days.

(21) Appl. No.: 11/952,883

(22) Filed: Dec. 7, 2007

(65) Prior Publication Data
US 2008/0200943 A1 Aug. 21, 2008

Related U.S. Application Data

(60) Provisional application No. 60/869,304, filed on Dec. 8, 2006.

(51) Int. Cl.
*A61M 29/00* (2006.01)
*A61B 17/34* (2006.01)

(52) U.S. Cl.
CPC .......... *A61B 17/3439* (2013.01); *A61B 17/3431* (2013.01)

(58) Field of Classification Search
CPC .......... A61B 17/3431; A61B 17/3439; A61M 25/0023; A61M 2025/0024; A61M 2025/0681; A61M 25/10; A61M 2025/1004; A61M 2025/1084; A61M 2025/1093
USPC .......... 606/191–195; 623/1.11–1.12
See application file for complete search history.

(56) References Cited

U.S. PATENT DOCUMENTS

| | | | |
|---|---|---|---|
| 6,053,313 A | | 4/2000 | Farrell et al. |
| 6,093,173 A | * | 7/2000 | Balceta et al. ........... 604/164.01 |
| 2003/0050658 A1 | * | 3/2003 | Trask et al. ................... 606/191 |
| 2005/0222576 A1 | | 10/2005 | Kick et al. |
| 2006/0052750 A1 | * | 3/2006 | Lenker et al. ............ 604/164.01 |
| 2006/0135962 A1 | * | 6/2006 | Kick et al. ..................... 606/108 |
| 2006/0135981 A1 | * | 6/2006 | Lenker et al. ................. 606/191 |
| 2008/0009887 A1 | * | 1/2008 | Cohn ............................ 606/151 |

OTHER PUBLICATIONS

International Search Report Application No. PCT/US2007/086865.

* cited by examiner

*Primary Examiner* — Katherine Rodjom
(74) *Attorney, Agent, or Firm* — Inskeep IP Group, Inc.

(57) ABSTRACT

An expandable medical sheath is configured to be introduced into a body in a first, low cross-sectional area configuration, and expanded to a second, enlarged cross-sectional configuration. The sheath is maintained in the first, low cross-sectional configuration by structures or elements within the sheath wall that maintain a collapsed shape. Upon expansion with a dilator, the sheath maintains a second, enlarged cross-sectional configuration by elements or structures within the sheath tubing wall that resist re-collapse. The sheath includes a nose cone or tapered fairing to deflect tissue from entering the collapsed distal end of the sheath during introduction. The fairing collapses following expansion and subsequent deflation of the dilator, thus allowing the tapered fairing to be withdrawn proximally through the central lumen of the sheath. In one application, the sheath is utilized to provide access for a diagnostic or therapeutic procedure such as percutaneous nephrostomy or urinary bladder access.

24 Claims, 11 Drawing Sheets

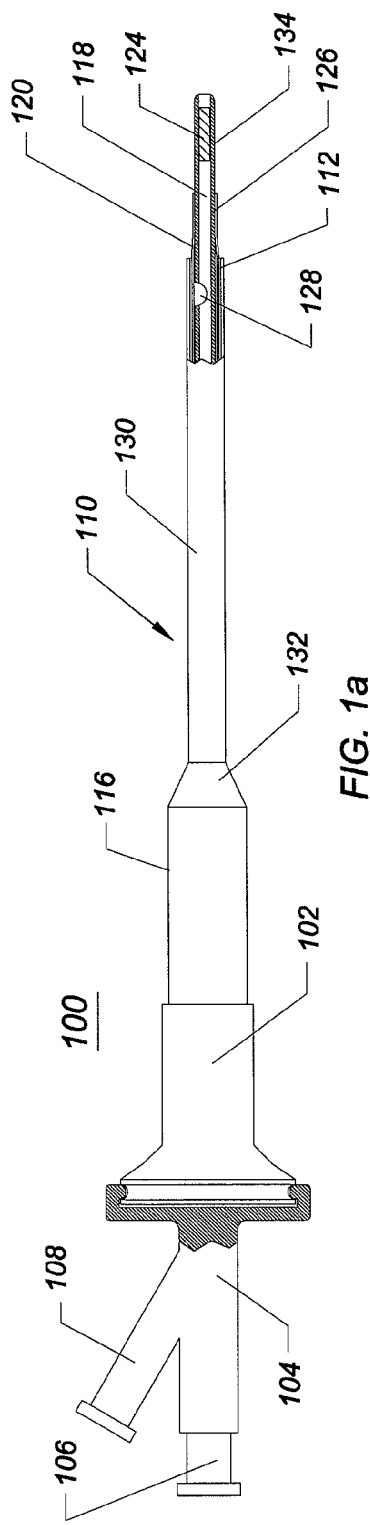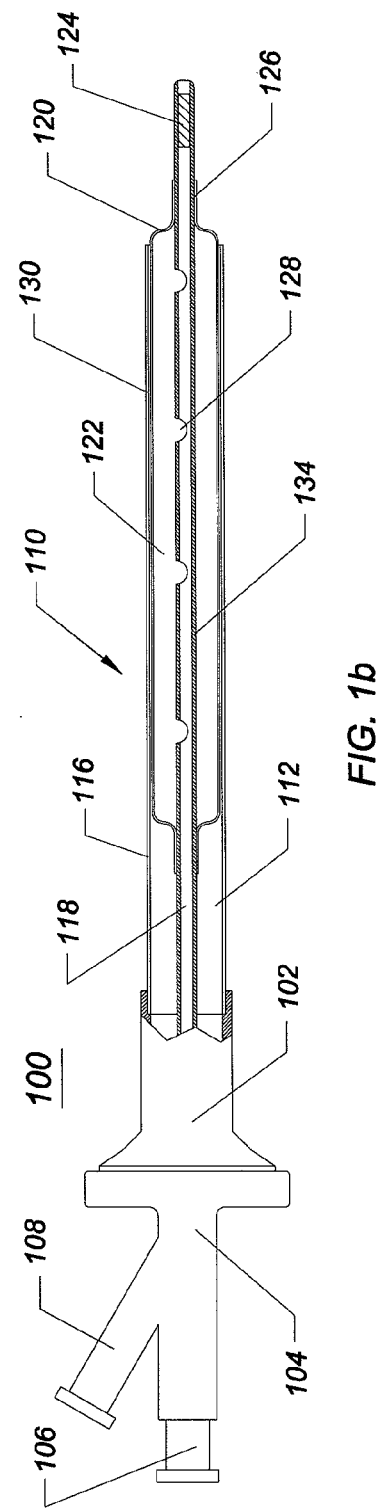

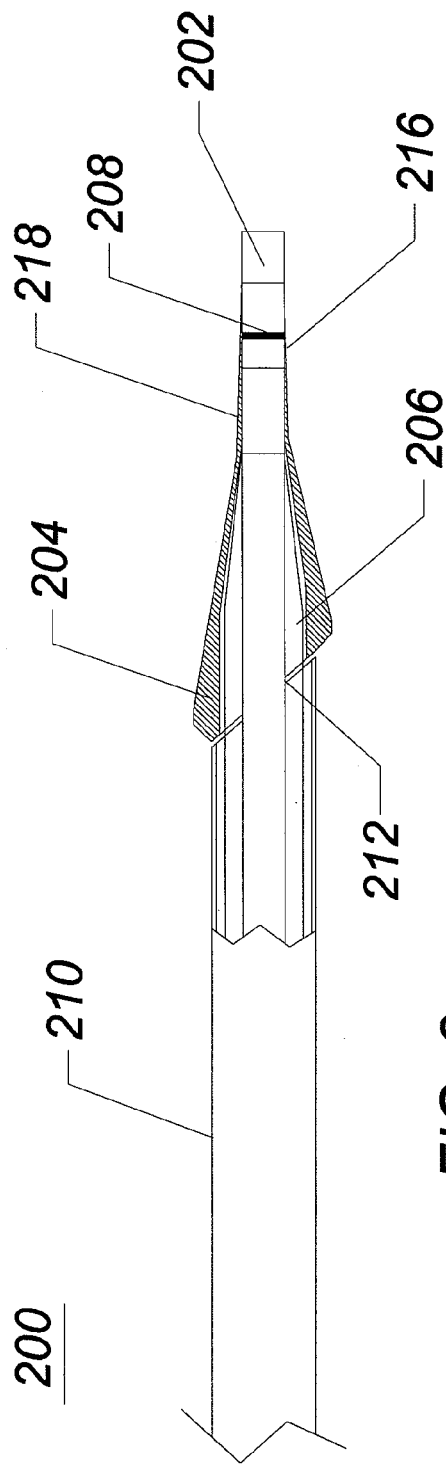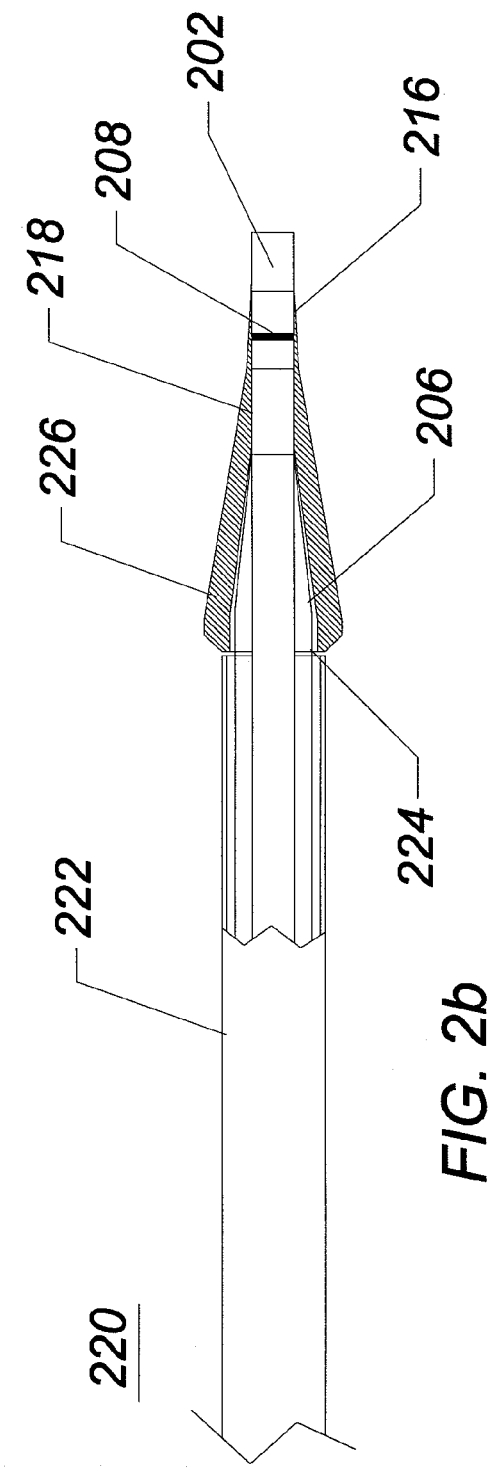
FIG. 2a
FIG. 2b

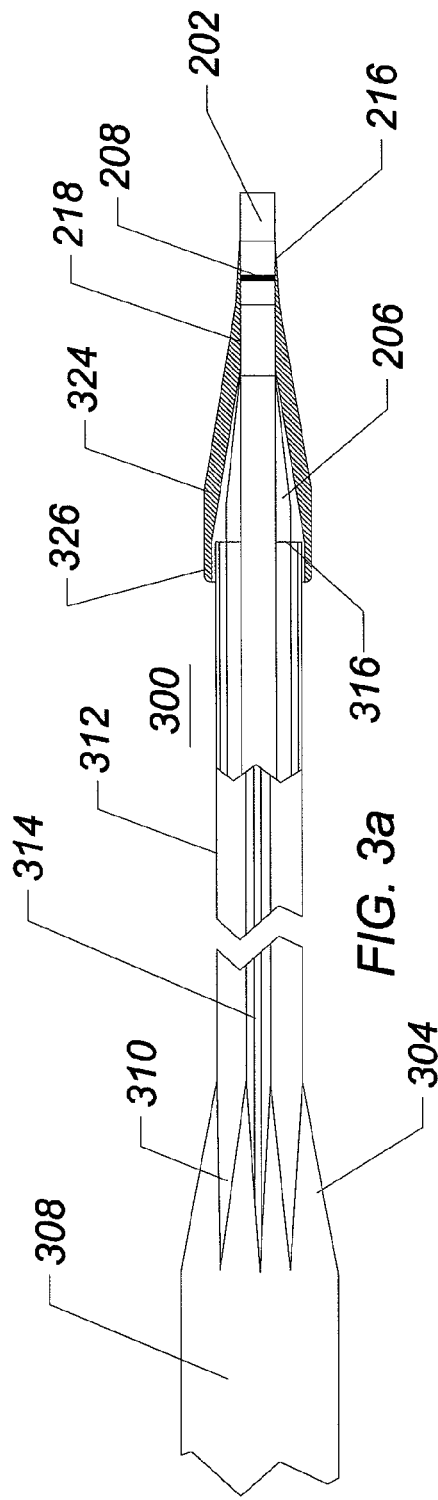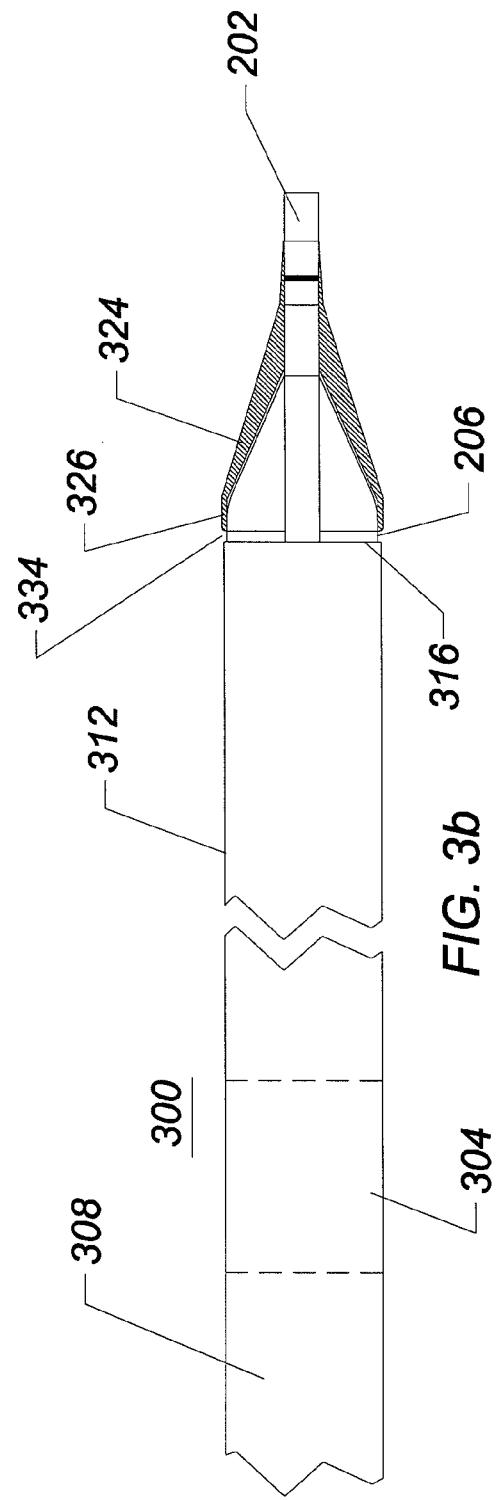

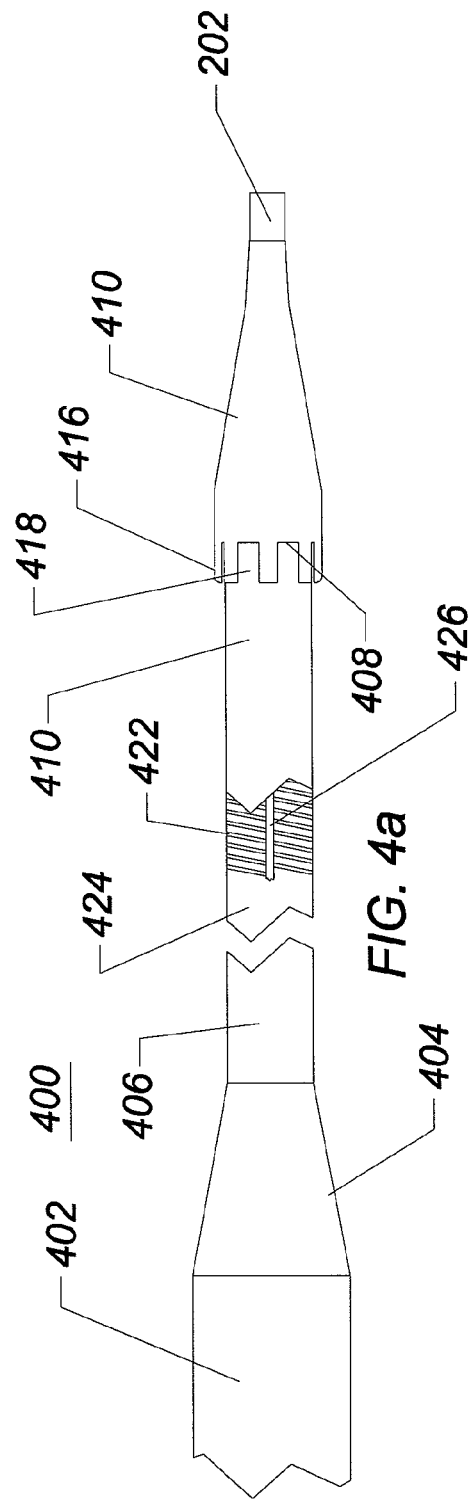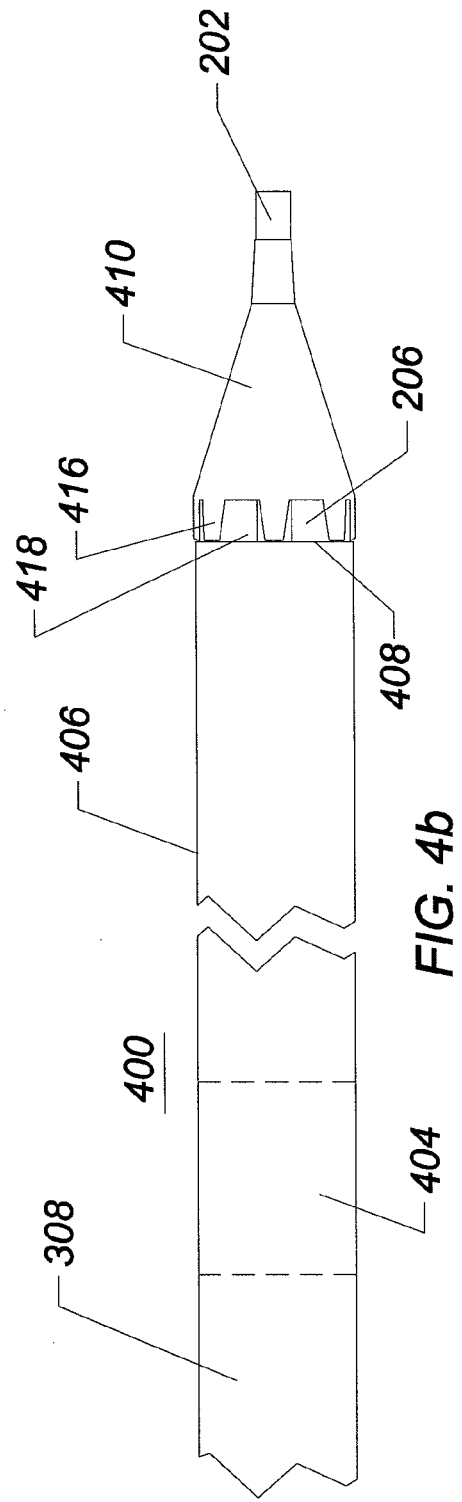
FIG. 4a
FIG. 4b

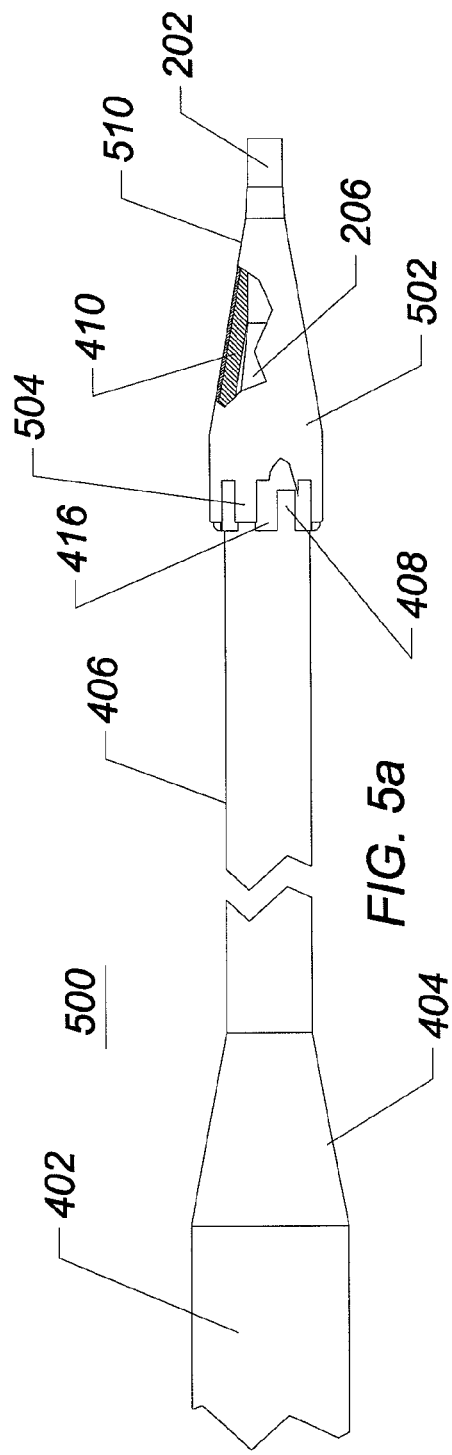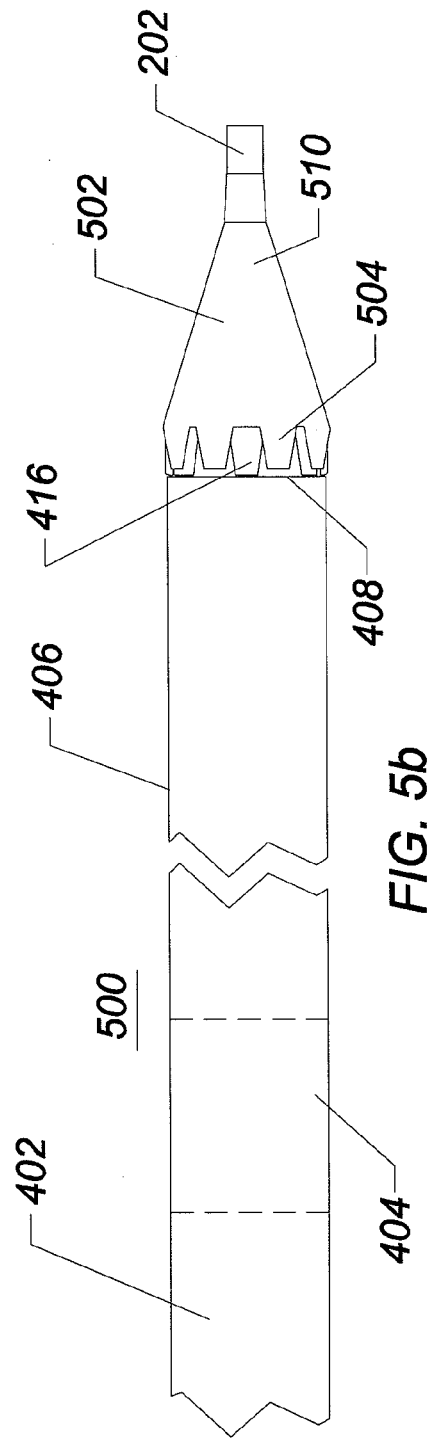

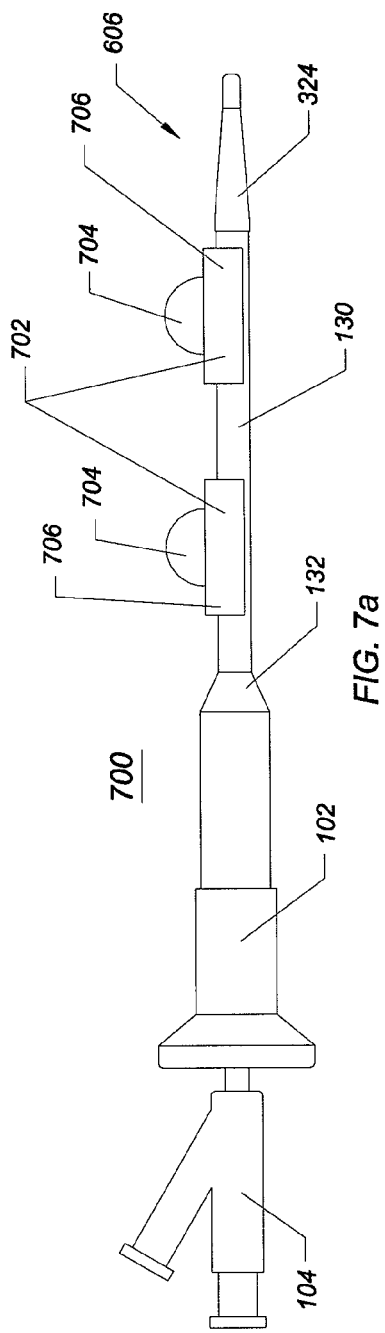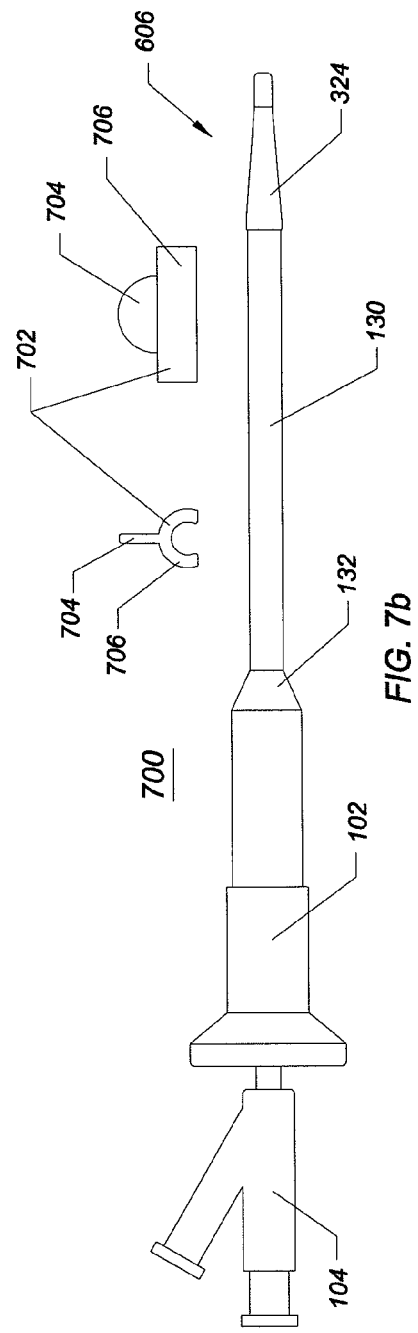

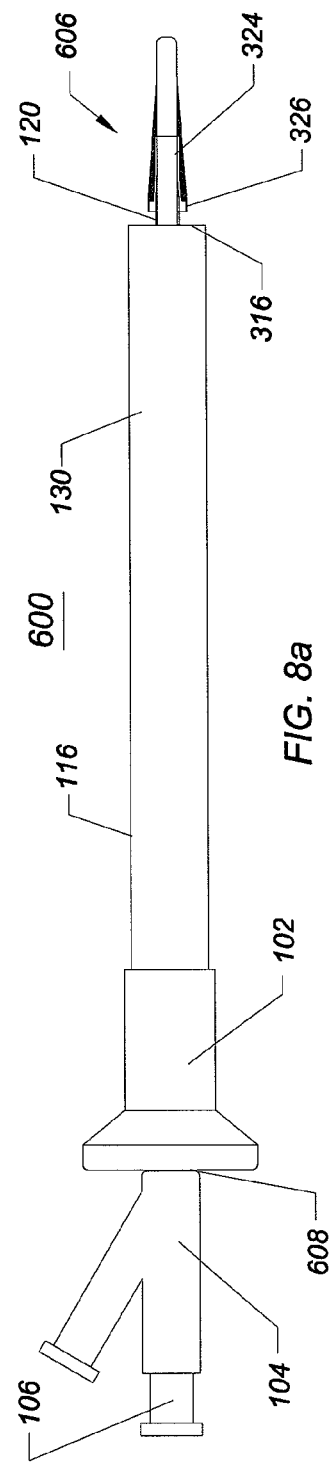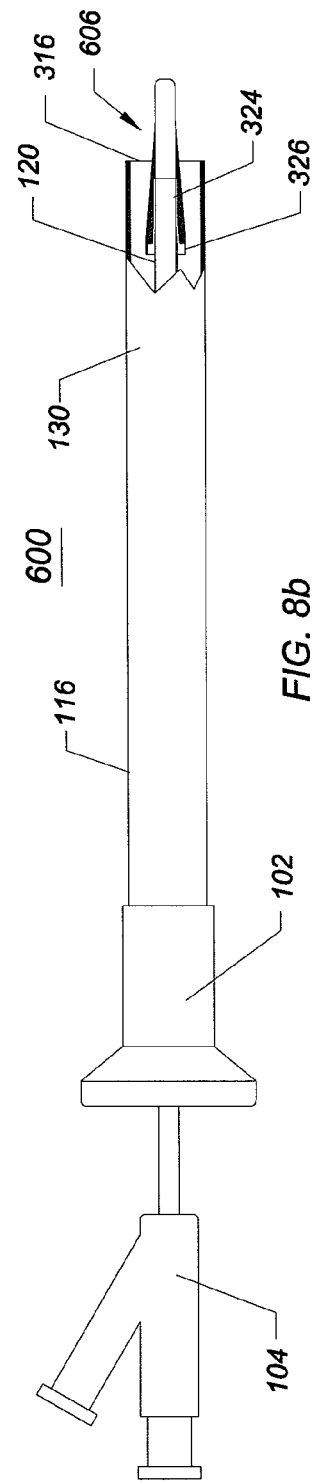
FIG. 8a
FIG. 8b

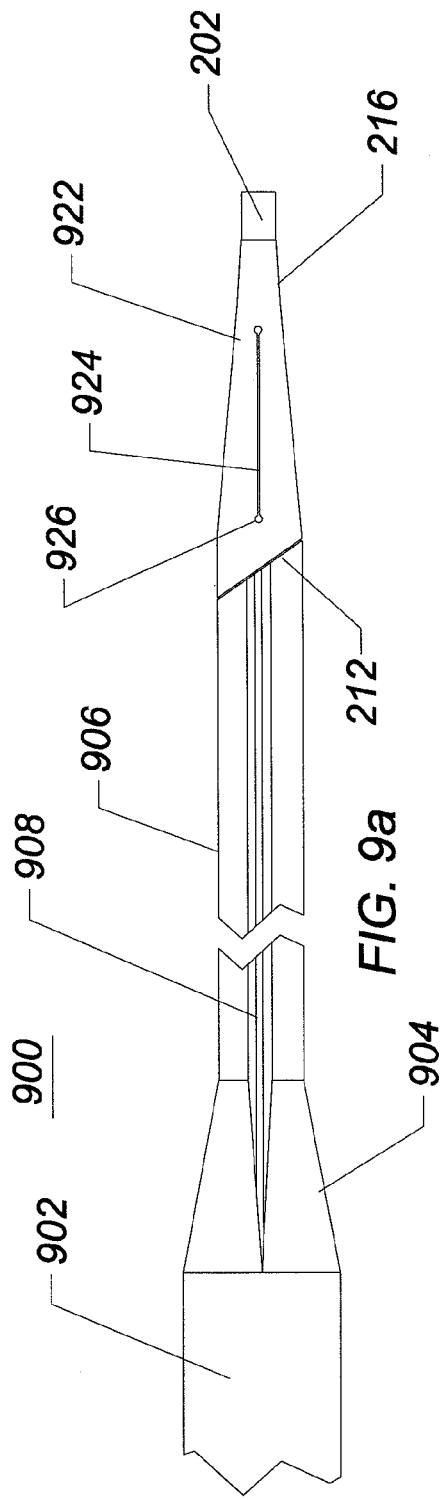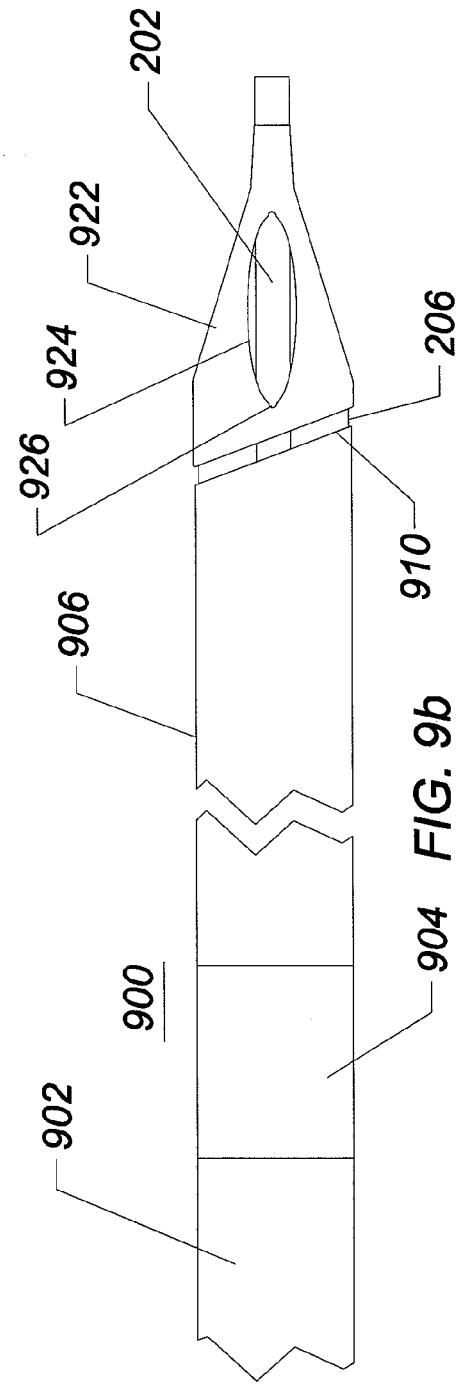

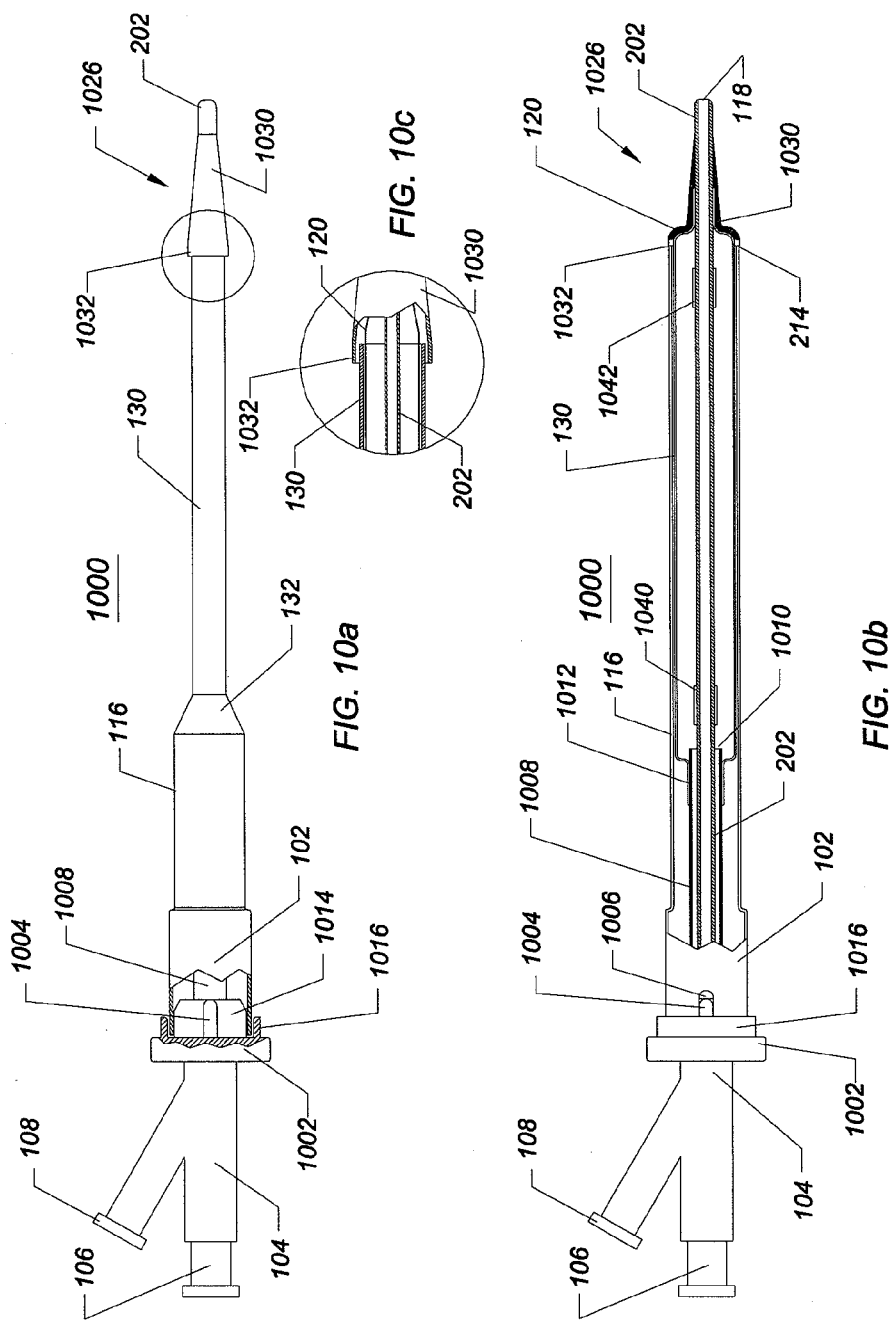

EXPANDABLE MEDICAL ACCESS SHEATH

CROSS-REFERENCE TO RELATED APPLICATIONS

This application claims the priority benefit of U.S. Provisional Application 60/869,304 filed Dec. 8, 2006, the entire contents of which are hereby incorporated by reference herein.

BACKGROUND OF THE INVENTION

1. Field of the Invention

The invention relates to medical devices and, more particularly, to methods and devices for forming a percutaneous channel.

2. Description of the Related Art

A wide variety of diagnostic or therapeutic procedures involves the introduction of a device through a natural or artificially created access pathway. A general objective of access systems, which have been developed for this purpose, is to minimize the cross-sectional area of the puncture, while maximizing the available space for the diagnostic or therapeutic instrument. These procedures include, among others, a wide variety of laparoscopic diagnostic and therapeutic interventional procedures.

Percutaneous nephrostomy is an example of one type of therapeutic interventional procedure that requires an artificially created pathway. Percutaneous nephrostomy is a minimally invasive procedure that can be used to provide percutaneous access to the upper urinary tract. At first, percutaneous nephrostomy was used only for urinary diversion but now it can be used for more complex procedures such as stone extraction, integrate endopyelotomy, and resection of transitional cell carcinoma of the upper urinary tract.

In many percutaneous nephrostomy systems, a stiff guidewire is first placed into the renal collection system through the renal parenchyma and the ureter under fluoroscopic control. A second "safety wire" may be placed with a dual lumen catheter for maintaining the tract should the first wire become dislodged or kinked.

Once guidewire control is established, a dilator sheath is used to create the tract and establish a rigid working lumen. One technique involves advancing a flexible, 8 French, tapered catheter over the first guidewire to provide guidewire protection as well as a stable path for the placement of larger diameter dilators and sheaths. The larger diameter sheaths are sequentially advanced over the catheter and each other until an approximately 34 French (11 to 12 mm diameter) tract is established. The inner sheaths or dilators may then be sequentially removed such that the outermost sheath defines a working lumen. In this system, tract formation is accomplished by the angular shearing force of each subsequent sheath placement, which cuts a path through the tissue. Because axial pressure is required to advance and place each sheath, care must be taken to avoid kinking the tapered catheter and/or advancing the sheaths too far and potentially perforating the renal pelvis. This technique requires a large number of steps, requires a large amount of force that can be readily misdirected, and is relatively time consuming.

A more recent technique utilizes a balloon that is advanced over the first guide wire. Once in place in the renal pelvis, the balloon is inflated with a dilute contrast media solution to enlarge the tract. Once the balloon is inflated to a suitable diameter, a rigid sheath is advanced over the balloon. Advancing the rigid sheath over the balloon typically requires applying axial force to the sheath as well as rotation of the sheath relative to the balloon. The balloon can then be deflated and removed from the rigid sheath so that the rigid sheath may define a working lumen. In general, this technique is considered less traumatic than the previously described technique of nested, concentric dilators. Nevertheless, placement of the rigid sheath still involves angular shearing forces and several steps. Expandable percutaneous sheaths have also been introduced to the market and these sheaths have the advantage of introduction at a small diameter and then being expanded to larger diameters for use. The use of a surrounding jacket has become standard when inserting expandable percutaneous access sheaths. The jacket surrounds and restrains the expandable portion of the sheath, and maintains the small diameter prior to and during insertion into the body. The presence of the jacket, which needs to be split or otherwise released, reduces the net expansion force of the sheath and compromises its function.

Additional information regarding percutaneous nephrostomy can be found in McDougall, E. Mo, et al. (2002), Percutaneous Approaches to the Upper Urinary Tract, Campbell's Urology, 8th ed, vol. 4, pp. 3320-3357, Chapter 98, Philadelphia, Saunders.

SUMMARY OF THE INVENTION

A need therefore remains for improved access technology, which allows a device to be percutaneously or transluminally passed through a small diameter tissue tract and then be expanded without artificial restriction by a system component.

An aspect in accordance with embodiments of the invention is a medical access system adapted for providing minimally invasive access to a biological body. The access system comprises an access sheath comprising an axially elongate tubular body that defines a lumen. At least a distal portion of the elongate tubular body is expandable from a first, folded, smaller cross-sectional profile to a second, greater cross-sectional profile to form an expanded distal portion of the access sheath. The access sheath has a distal edge. A dilator is slidably disposed within the lumen of the axially elongate tubular body. The dilator has a first, non-expanded configuration. The dilator has a second, expanded configuration, which is capable of expanding the first, folded smaller, cross-sectional profile of the access sheath into the second, greater cross-sectional profile of the access sheath. A tapered distal fairing affixed to the dilator shields the distal edge of the access sheath from tissue as the sheath is being advanced distally into the body. A proximal end of the tapered distal fairing has an inside diameter that expands to approximately the same diameter as the outside diameter of the dilator when the dilator is in its expanded configuration and that has an outside diameter that contracts to a diameter smaller than an inside diameter of the expanded distal portion of the access sheath when the dilator collapses to a collapsed configuration.

One embodiment of the invention comprises a medical access system for providing minimally invasive access. The system includes an access sheath comprising an elongate tubular body that defines a lumen, at least a portion of the elongate tubular body being expandable from a first, folded, smaller cross-sectional profile to a second, greater cross-sectional profile. The expandable region of the sheath is capable of maintaining, without external constraint, its collapsed configuration when folded into a first, smaller cross-sectional diameter.

In another embodiment of the invention, a medical access system for providing minimally invasive access includes an introduction sheath comprising an elongate tubular body having a proximal end and a distal end and defining an axial lumen. At least a portion of the elongate tubular body is expandable from a first, smaller cross-sectional profile to a second, greater cross-sectional profile. This expandable region can be advantageously located at or near the distal end of the elongate tubular body. The length of the expandable region can range from less than 5% to substantially 100% of the working length of the elongate tubular body. The medical access system includes a dilator capable of expanding the expandable region from a first, smaller cross-sectional area to a second, larger cross-sectional area.

In another embodiment of the invention, a medical access sheath assembly for providing minimally invasive access comprises an access sheath that includes an elongate tubular member having a proximal end and a distal end, wherein the space interior to the tubular wall defines a working lumen. At least a portion of the elongate tubular member is expandable from a first, folded, smaller cross-sectional profile, or diameter, to a second, greater cross-sectional profile or diameter. The sheath can include a dilator capable of expanding the expandable region from its first, smaller cross-sectional diameter to a second, larger cross-sectional diameter. The dilator can include, at or near its distal end, a tapering or conical nose cone. The nose cone leads the folded sheath as it is inserted into the body and substantially prevents, deflects, or blocks tissue from impinging on the distal edge of the folded sheath. The nose cone can be elastomeric or it can be a rigid structure. The nose cone can be configured to be hollow along at least a portion of its most proximal region. The nose cone can be configured to extend up to but not extend proximally to the distal end of the sheath. The nose cone can be configured to extend, in part or around its entire circumference, to a point proximal to the distal end of the sheath. The nose cone can comprise a skirt that loosely is disposed proximally of the distal end of the sheath so as not to impart any restrictive radially directed inward force on the smaller cross-sectional profile sheath. The skirt can form a continuous circumferential shape or it can form an undulating shape with fingers extending proximally from the attachment point of the skirt to the nose cone. The skirt can comprise separate overlapping fingers so that there are no unprotected sheath distal edges exposed between the fingers. On retraction, the fingers would retain little or no hoop strength and would therefore be easily withdrawn with proximal motion of the expandable member relative to that of the axially elongate tubular body, or sheath.

Another embodiment of the medical access system for providing minimally invasive access includes an elongate tubular body that defines a lumen extending from its proximal end to its distal end, at least a portion of the elongate tubular body being expandable from a first, folded, smaller cross-sectional profile to a second, greater cross-sectional profile. An expandable member is positioned within the elongate tubular body and configured to expand the elongate tubular body from the first, smaller cross-sectional profile to the second, greater cross-sectional profile. A tapered fairing is affixed to the expandable member proximate its distal tip. A stop can be provided, preferably at the proximal end of the axially elongate tubular structure to limit distal movement of the expandable member, and the tapered fairing, as the elongate tubular body is manipulated into the body. The stop can be configured to engage a hub or other feature on the proximal end of the axially elongate tubular structure and further engage a feature on the proximal end of the dilator such that the dilator and the axially elongate tubular structure are axially constrained not to move relative to each other. The stop can be configured to be removable or releasable to permit selective axial relative movement between the dilator and the axially elongate tubular body when dilator removal is desired. In an embodiment, the dilator comprises an axially elongate shaft that extends substantially from its proximal end to its distal end. The dilator shaft can comprise elements that prevent stretching to prevent the tapered fairing at the distal tip from moving relative to the distal end of the sheath or elongate tubular body even when the stop is engaged at the proximal end of the device. Such anti-stretch elements can comprise non-stretchable tubing materials or a co-extruded line or tube of a material such as polyamide.

In another embodiment of the invention, a medical access assembly includes an elongate tubular body that defines a lumen. At least a portion of the elongate tubular structure is expandable from a first, folded, smaller cross-sectional profile to a second, greater cross-sectional profile. An expandable member is positioned within the elongate tubular body and configured to expand the elongate tubular body from the first, smaller cross-sectional profile to the second, greater cross-sectional profile. A tapered fairing is affixed to the expandable member proximate its distal tip. The tapered fairing can be elastomeric and expand radially with the expandable member. Following collapse of the expandable member, the tapered fairing, being elastomeric collapses with the expandable member to a diameter smaller than that of the expanded elongate tubular structure. In a further embodiment, the tapered fairing is forced forward toward the distal end of the expandable member, said forward movement facilitating disengagement between the tapered fairing and the distal end of the expandable region of the sheath.

In another embodiment of the invention, a medical access sheath system includes an elongate tubular structure that defines an lumen, at least a portion of the elongate tubular structure being expandable from a first, folded, smaller cross-sectional profile to a second, greater cross-sectional profile. A packaging protector is provided which covers at least a portion of the expandable region of the sheath, said packaging protector being removable prior to use of the device. The packaging protector serves as a temporary retaining sleeve, retaining clip, or "C-clip", which is removed prior to inserting the sheath into a patient or mammalian body.

In another embodiment, a medical access sheath system comprises an axially elongate tubular structure having a proximal end and a distal end. At least a portion of the distal region of the axially elongate tubular structure is expandable and compressible and comprises a composite wall with malleable elements embedded therein. The malleable composite wall can be fabricated using a polymer exterior and interior layer with a central reinforcing layer of malleable material such as annealed stainless steel sandwiched therebetween. The malleable expandable region eliminates the need for a jacket to constrain or maintain the expandable region in its compressed configuration and provides additional strength in the dilated or expanded configuration. The malleable structure exerts a force greater than the elastomeric forces applied by the polymeric structure but is unable to resist expansion forces generated by a dilator such as a high pressure balloon or the like.

In another embodiment of the invention, a method of providing medical access comprises inserting a guidewire into a patient, percutaneously inserting an elongate tubular body having a first, smaller cross-sectional profile over a guidewire such that tissue is diverted from impinging on the distal edge of the elongate tubular body; expanding the elongate tubular body from the first, smaller cross-sectional profile to a second, greater cross-sectional profile; removing the expandable member from the elongate tubular body; performing diagnostic or therapeutic intervention through the elongate tubular body; and removing the elongate tubular body from the patient. In yet another embodiment, the elongate tubular body is inserted into the patient without the use of a guidewire. In this embodiment, the guidewire can be eliminated or it can be replaced with a trocar or core device, such as a hollow needle or a Veirass needle, which can be permanent or removable.

In another embodiment of the invention, a medical access sheath system comprises an elongate tubular body that defines a lumen. At least a portion of the elongate tubular structure is expandable from a first, folded, smaller cross-sectional profile to a second, greater cross-sectional profile. In an embodiment, a tapered tip is provided to aid in the insertion of the sheath by forming a smooth transition from the dilator tip to the sheath distal end. The tapered tip is configured to protect the sheath distal end from the ingress of tissue during insertion, said tissue ingress potentially causing the sheath to hang-up or prematurely dilate. The tapered tip is configured to protect the dilator, balloon, or expandable member from sharp or boney tissue and hardened calculi during insertion and positioning. In an embodiment, the transition forms a gradual taper increasing in diameter from the distal most aspect to a more proximal aspect. Such a gradual transition within the tapered tip increases the tactile signal, or force feedback, from the sheath tip to the surgeon during manual insertion and positioning. In an embodiment, the tapered tip can be coated with a hydrophilic lubricious coating to minimize friction between the tip and surrounding tissue during introduction into the patient.

In one embodiment, where the medical access sheath is used to provide access to the upper urinary tract, the medical access sheath may be used to provide access by tools adapted to perform biopsy, urinary diversion, stone extraction, antegrade endopyelotomy, and resection of transitional cell carcinoma and other diagnostic or therapeutic procedures of the upper urinary tract or bladder. An expandable device that does not include a restraining jacket permits a substantially increased force to be supplied to dilate the expandable region of the sheath against the radially inwardly directed tissue forces. The embodiments disclosed herein, which represent unrestrained expandable sheaths, permit increased expansion forces of 33% or more relative to sheaths that are constrained or restrained by a jacket, given the same amount of inflation force or pressure. The expandable sheaths disclosed herein comprise wall structures that are plastically deformable or malleably deformable. These sheath structures do not comprise walls that are elastomeric or resilient and thus will hold their shape once set in a certain configuration.

Other applications of the medical access sheath include a variety of diagnostic or therapeutic clinical situations, which require access to the inside of the body through either an artificially created or natural body lumen. Such applications include, but are not limited to, ureteral access, urethral access, endovascular access, endogastric access, and the like.

In addition, all of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 1a is a partial breakaway side elevation of a medical access sheath and dilator in the unexpanded configuration, according to an embodiment of the invention;

FIG. 1b is a partial breakaway side elevation of a medical access sheath and dilator in the expanded, large cross-sectional configuration, according to an embodiment of the invention;

FIG. 2a is a side cross-sectional view of the distal end of a medical access sheath comprising a tapered fairing tip that butts against, but does not extend proximal to, a beveled distal end of the sheath, according to an embodiment of the invention;

FIG. 2b is a side cross-sectional view of the distal end of a medical access sheath comprising a tapered fairing tip that butts against, but does not extend proximal to, a perpendicularly cut distal end of the sheath, according to an embodiment of the invention;

FIG. 3a is a side cross-sectional view of a medical access sheath comprising a tapered fairing tip that extends slightly proximal to the distal end of the sheath, according to an embodiment of the invention;

FIG. 3b illustrates a cross sectional view of a medical access sheath comprising a tapered fairing tip that overlaps, or extends proximal to, the distal end of the sheath, wherein the expandable portion of the sheath has been dilated, according to an embodiment of the invention;

FIG. 4a is a side view of an the distal end of an unexpanded medical access sheath comprising a tapered fairing tip with fingers that extend proximal to the distal end of the sheath, according to an embodiment of the invention;

FIG. 4b is a side view of the distal end of the expanded medical access sheath comprising the tapered fairing tip with fingers that initially extended proximal to the distal end of the sheath but which now have been stretched distally, according to an embodiment of the invention;

FIG. 5a is a side view of the distal end of an unexpanded medical access sheath comprising a tapered fairing tip with a double layer of fingers that extend proximal to the distal end of the sheath, wherein the two layers of fingers are offset to fill any spaces therebetween, according to an embodiment of the invention;

FIG. 5b is a side view of the distal end of the expanded medical access sheath comprising the tapered fairing tip and a plurality of layers of overlapping fingers that have stretched distally following expansion, according to an embodiment of the invention;

FIG. 7a is a side view of a radially compressed medical access sheath comprising removable packaging protectors for the expandable region, according to an embodiment of the invention;

FIG. 7b illustrates the radially compressed medical access sheath with the removable packaging protectors having been removed and one of the protectors rotated to present an end view, according to an embodiment of the invention;

FIG. 8a is a side, partial cutaway, view of the medical access sheath in which the dilator has been re-collapsed after expanding the sheath and which shows distal advancement of the dilator, relative to the sheath, according to an embodiment of the invention;

FIG. 8b illustrates a partial cross-sectional view of the expanded medical access sheath of FIG. 8a with the deflated dilator being withdrawn proximally, according to an embodiment of the invention; and FIG. 9a illustrates a side view of an expandable medical access sheath and dilator comprising a fairing tip having a longitudinal slit to facilitate retraction, according to an embodiment of the invention;

FIG. 9b illustrates the expandable medical access sheath of FIG. 9a with the fairing tip expanded away from the end of the sheath;

FIG. 10a illustrates a partial breakaway side view of an unexpanded medical access sheath and dilator comprising a tapered fairing having a proximal edge that loosely overlaps the distal edge of the sheath tubing, according to an embodiment of the invention;

FIG. 10b illustrates a partial breakaway side view of the medical access sheath of FIG. 10a following expansion, according to an embodiment of the invention; and FIG. 10c illustrates an enlarged partial cross-sectional view of the distal edge of the access sheath and the proximal portion of the tapered fairing bounded by the circle in FIG. 10a.

DETAILED DESCRIPTION OF THE PREFERRED EMBODIMENT

Figure 1C:
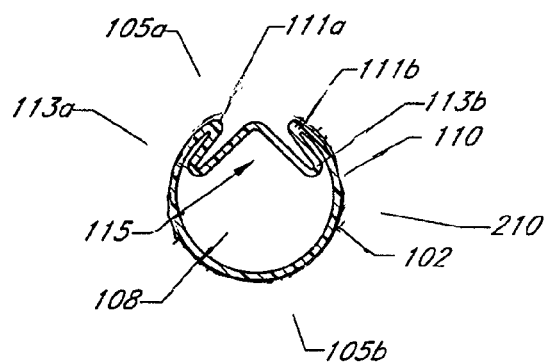
FIG. 1c is a schematic lateral cross-sectional illustration of an exemplary embodiment of a folding profile for the sheath.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

In embodiments described herein, a medical access sheath, which is sometimes generally termed a catheter, sheath, or introducer, which can be an axially elongate hollow generally tubular structure having a proximal end and a distal end. The axially elongate structure can have a longitudinal axis and can have an internal through lumen that extends from the proximal end or portion to the distal end or portion of the structure for the passage of instruments, fluids, tissue, or other materials. As is commonly used in the art of medical devices, the proximal end or portion of the device is that end that is closest to the user, typically a surgeon or interventionalist. The distal end or portion of the device is that end closest to the patient, or the end that is first inserted into the patient. A direction being described as being proximal to a certain landmark will be closer to the user, along the longitudinal axis, and further from the patient than the specified landmark. The diameter of a catheter is often measured in "French Size" which can be defined as 3 times the diameter in millimeters (mm). For example, a 15 French catheter is 5 millimeters in diameter. The French size is designed to approximate the circumference of the catheter in mm and is often useful for catheters that have non-circular cross-sectional configurations. While the original measurement of "French" used $\pi$ (3.14159 . . . ) as the conversion factor between diameters in millimeters (mm) and French, the system has evolved today to where the conversion factor is 3.0. While in many embodiments the tubular structure has a substantially round cross-section, in other embodiments the tubular structure can have a non-round (e.g., oval, square, etc.) cross-sectional shape.

FIG. 1a is a partial breakaway side view of an embodiment of a medical access sheath 100. The sheath 100 generally comprises an elongate tubular body 110 with an axial lumen 112, and is designed to provide medical access to a site in the body for the purpose of diagnosis or treatment. In the illustrated embodiment, the medical access sheath 100 generally comprises a sheath hub 102, a proximal non-expandable region 116, a transition zone 132, a distal expandable region 130, a dilator hub 104, a balloon inflation port 108, a guidewire access port 106, a dilator tube 134 having a dilator lumen 118, a guidewire valve 124, a balloon 120, a distal balloon bond 126, and one or more balloon inflation skives 128. These components will be described in more detail below.

As shown in FIG. 1a, the axially elongate tubular body 110 forms a wall that can encompass or define, at least in part, the axial lumen 112. The axial lumen 112 can extend from the proximal end or portion to the distal end or portion of the axially elongate tubular body 110. The sheath hub 102 can be affixed or coupled to the proximal end of the axially elongate tubular body 110 and the lumen of the sheath hub can be operably connected to the axial lumen 112 within the tubular body 110. The proximal non-expandable region 116 of the axially elongate tubular body 110 can be affixed or coupled to the distal expandable region 130 of the tubular body 110 by the transition zone 132. The central lumens of the proximal region 116, the distal region 130, and the transition zone 132 are operably coupled together. The dilator components (e.g., the dilator tube 134 and balloon 120) are preferably axially, slidably movable and removable within the axially elongate tubular body 110. The dilator hub 104 can be coupled to the proximal end of the dilator tube 134 and the lumens of the dilator hub 104 are preferably operably connected to the lumens 118 within the dilator tube 134. The balloon inflation port 108 is coupled to the dilator hub 104 and is operably connected to a dilator lumen or annulus (not shown) within the dilator tube 134. The guidewire access port 106 is coupled to the dilator hub 104 and is operably connected to the through lumen 118 within the dilator tube 134. The dilator balloon 120 can be coupled at each end to the dilator tube 134 with a proximal balloon bond (not shown) and a distal balloon bond 126. A plurality of skives 128 penetrate the dilator tube 134 at the wall between the balloon inflation lumen or annulus (not shown) and the exterior of the dilator tube 134 in the region under the balloon 120. Alternatively, the balloon 120 interior is operably connected to a balloon inflation annulus (not shown) which is concentrically formed by an inner and an outer dilator tube wherein the balloon 120 has its proximal bond (not shown) bonded to the outer dilator tube near the distal end of the outer dilator tube. In this alternative embodiment, the inner dilator tube comprises the through lumen 118 and is attached to the balloon 120 with the distal balloon bond 126.

The length and diameter of the axially elongate tubular body 110 can be varied according to clinical need, as will be understood by those skilled in the art with reference to this disclosure. In an exemplary embodiment for percutaneous nephrostomy, the access sheath 100 has an overall working length (the length of tubular body 110 that projects proximally of the sheath hub 102) in a range from about 17 centimeters to about 55 centimeters with the distal section 130 having a length in a range from about 4 centimeters to about 30 centimeters. A portion or all of the distal section 130 is expandable from a first, smaller cross-sectional profile to a second, larger cross-sectional profile. The first, smaller cross-sectional profile of the distal section 130 eases its insertion into a treatment site or lumen. After insertion, the distal section 130 is expanded to a second, larger cross-sectional profile to provide a larger passageway for surgical instruments to reach the percutaneous treatment site.

For percutaneous nephrostomy, the smaller cross-sectional profile may have a diameter in a range from about 8 French to about 24 French and the larger cross-sectional profile may have a diameter in a range from about 10 French to about 40 French. In the larger cross-sectional profile, the lumen 112 may have a diameter in a range from about 8 French to about 38 French. The deployment catheter or dilator, comprising the balloon 120, the tubing 134, and the hub 104, is inserted into the lumen 112 of the medical access sheath 100 such that the balloon 120 is arranged within the distal section 110. The balloon 120 may then be inflated to expand the distal section 130 from its first, smaller cross-sectional profile to its second, larger cross-sectional profile following the insertion of the medical access sheath 100 into a treatment site.

In the illustrated embodiments described herein, the distal section 130 can achieve its smaller profile by providing the distal section with one, two, three or more longitudinal folds (see e.g., FIGS. 1C-1D), which reduce the cross-sectional area. As the distal section is unfolded, the cross-sectional area increases. In other embodiments, the distal section can be formed from a material that deforms or stretches to a larger cross-sectional area and thus need not be folded in the smaller cross-sectional configuration.

Figure 1D:
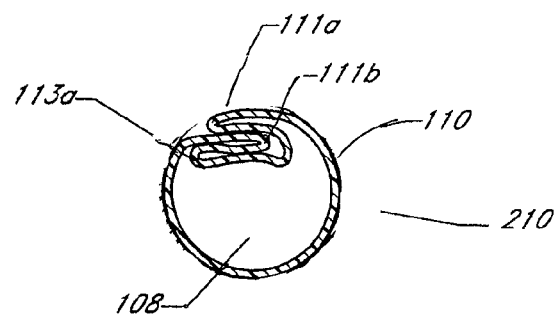
FIG. 1d is a schematic lateral cross-sectional illustration of another embodiment of a folding profile for the sheath.

FIG. 1C is a lateral cross-sectional view of the sheath and illustrates a folding profile for collapsing the distal section into a smaller cross-sectional profile. In this embodiment, the distal section includes two creased outer sections 111a, 111b that lie on the perimeter of the tubing 102 and generally face each other. Two creased inner sections 113a and 113b lie within the perimeter of the tubing 102 and generally face away from each other. An additional fold or crease (not shown) may be formed on the section 115 of the tubing between the two outer creased sections 111a, 111b.

FIG. 10 is also a lateral cross-sectional view of the sheath. FIG. 38 illustrates a modified folding profile for collapsing the distal section 110 into a smaller cross-sectional profile. As shown in the figure, the outer creased sections 111a, 111b are overlapped with each other. In one embodiment, only a portion of the outer creased sections 111a, 111b are overlapped with each other. For example, the distal edge of the outer creased sections and adjacent portions may be over lapped with each other.

FIG. 1b shows a partial breakaway view of the sheath 100 following inflation of the balloon 120. The sheath 100 comprises the sheath hub 102, the dilator hub 104, the guidewire access port 106, the balloon inflation port 108, the balloon 120, and the length of dilator tubing 134. The sheath tube 110 further comprises the non expendable sheath region 116, the expandable sheath region 130, and the transition zone 132. The balloon 120 has a central balloon area 122. The length of dilator tubing 134 further comprises a central lumen 118, the plurality of skives 128, the distal balloon bond 126, and the guidewire valve 124.

As shown in FIG. 1b, in the illustrated embodiment, the sheath tube 110 is a composite structure with three distinct regions—the proximal nonexpendable sheath region 116, the transition zone 132, and the distal expandable sheath region 130. The proximal sheath region 116, the transition zone 132, and the expandable sheath region 130 coupled to each other with the transition zone 132 providing a smooth exchange between the properties of the proximal nonexpendable sheath region and the distal expandable sheath region 130. The balloon 120 can be bonded or coupled to the dilator tubing 134 at the distal bond area 126 and the proximal bond area (not shown). The plurality of skives 128 are visible in this cutaway illustration. The skives 128 are openings in the balloon inflation lumen 118 that permit inflation of the balloon through the balloon inflation lumen. The balloon 120 comprises an internal volume or central balloon area 122 into which a fluid, preferably liquid, is injected under pressure to inflate the balloon 120 and dilate the expandable region 130.

As shown in FIGS. 1a and 1b, in an embodiment for percutaneous nephrostomy, the distal section 130 is placed into the renal collecting system through the renal parenchyma and ureters. The length of the distal section 130 is thus determined by the anatomy and is generally in a range from about 11 centimeters to about 30 centimeters. In the illustrated embodiment, the proximal end 116 of the tubing 110 is flared and fitted onto the dilator tubing 134 with the dilator tube 134 being concentrically constrained within the sheath tubing 110. The overall length of the sheath tubing 110 depends on the distance between the insertion and treatment locations, and is generally in a range from about 10 centimeters to about 100 centimeters for various clinical indications. As mentioned above, for percutaneous nephrostomy, the length of the tubing is approximately 11-30 centimeters. In this embodiment, the sheath hub 102 is omitted to permit cross-sectional deformation of the proximal end 116 of the sheath tubing 110 to permit calculi with a single dimension greater than the diameter of the tubing 110 to be withdrawn therethrough. In this embodiment, the dilator hub 104 can be provided with a pin, projection, or other locking means to engage with a slot or hole in the proximal region 116.

As shown in FIGS. 1a and 1b, in the illustrated embodiment, the medical access sheath 100 comprises a length of tubing 110, which defines a lumen 112. In the expanded configuration, the tubing 110 has sufficient structural integrity to support the surrounding tissue and provide a working lumen to facilitate instrument maneuvering and visualization within the internal structure of the tissue or organ under examination or treatment. The structural integrity of the tubing 110 is determined by a combination of factors including but not limited to, material, wall thickness to diameter ratio, yield strength, elongation at yield, and the like.

In an embodiment, the tubing 110 is also sufficiently pliable that the cross-sectional shape of the lumen 112 can change in response to the shape of objects drawn therethrough. The tubing may also be substantially inelastic, in which case the cross-sectional area of the expanded lumen remains constant, but the shape of the lumen will vary to accommodate tools (e.g., graspers) and objects (e.g., stones) advanced therethrough. This arrangement facilitates the passage of unsymmetrical objects that have a maximum diameter that is larger than the inner diameter of the tubing 110 in the expanded condition, so long as an outer perimeter of the object is no greater than the inside perimeter (e.g., the French size) of the lumen 112. In this arrangement, the tubing is substantially inelastic. As such, the inside perimeter of the expanded lumen remains constant relative to its undistorted configuration, but the tubing 110 reconfigures as an object exerts an outward force against the tubing 110. For example, for some unsymmetrical objects the tubing 110 assumes an elliptical shape with a major axis in a first direction that increases as a minor axis in a second direction decreases. In one embodiment, the tubing 110 may reconfigure along one or more of the creases or folds formed on the distal section 130.

In an alternative embodiment, or in combination, the tubing 110 can also compress and/or expand elastically to allow passage of an unsymmetrical object with a maximum diameter larger than the diameter of the working lumen 112. As the unsymmetrical object is passed through the lumen 112, an outwardly directed force exerted by the unsymmetrical object causes the diameter of the lumen 112 to increase along one axis while the diameter decreases along another axis to allow passage of the unsymmetrical object. The use of an elastic or resilient material for the tubing 110 will thus allow both the reconfiguration of lumen 112 shape as discussed above as well actual enlargement of the cross-sectional area of the lumen 112 in either a circular or non-circular profile. As the lumen 112 is reconfigured, the tubing 110 may compress and/or expand elastically along one or more of the creases or folds formed on the distal section 130.

The tubing is preferably also formed from a material that provides a low coefficient of friction or high lubricity. The tubing may comprise PTFE, FEP, nylon, PEBAX, polypropylene, polyethylene, polyurethane, polyester, silicone, or other suitable materials. Alternatively, any of a variety of lubricious coatings, including silicone oil and hydrophilic materials, often polyurethane-based, may be applied to the inside and/or outside surface of the tubing 102. Polymeric coatings can include PTFE, FEP, parylene, and others known in the art.

In one exemplary embodiment, the tubing 110 comprises PTFE and has a wall thickness from about 0.010 inches to about 0.024 inches. In one embodiment configured for nephrostomy, the tubing 102 comprises PTFE, and has an outer diameter of about 33 French and a wall thickness of about 0.019 inches. The wall thickness to diameter ratio is approximately 0.044 to about 1 in this embodiment. In another embodiment, suitable for ureteral access, the tubing diameter is about 0.210 inches (16 French) and the wall thickness is in a range from about 0.009 to 0.010 inches.

It should be appreciated that the physical properties of the tubing 110 described above represent only some optimized arrangements. Due to the interplay of the length, material, thickness, number of folds and possibly other physical characteristics of the tubing, the preferred characteristics of the tubing 110 cannot be described in terms of a specific set of variables. To the contrary, changes in any one variable may be offset by commensurate changes in another variable, to produce an effective tubing 110 that provides one or more of the advantages described above. Such optimization can be accomplished through routine experimentation by those of skill in the art in view of the disclosure herein, and in view of the objective of providing a tubular sheath with one or more of the properties described above. In addition, the physical properties of the tubing 110 are dependent on the environment of use. For example, the structural integrity of the tubing 110 is often a function of the pressure exerted by the surrounding tissue as well as the temperature of the operational surroundings, in this case at or near a body temperature of 37 degrees centigrade.

As shown in FIG. 1*a*, the inner tube 134 preferably extends the entire length of the sheath system 100. A guide wire lumen 118 is defined by the interior of the inner tube 134. The dilation or expansion catheter assembly can travel along a guide wire extending through the guide wire lumen 118. The inner tube 134 can carry coaxially on its exterior an outer tube (not shown). The outer tube (not shown) terminates proximally into the distal end of the dilator hub 104, and distally into a balloon 120 such that the space or annulus between the inner tube 134 and the outer tube (not shown) forms an inflation lumen for the balloon 120. The balloon 120 advantageously comprises any of a variety of suitable materials, such as, for example, PET, copolymers of polyester, Nylon, PEBAX, Polyurethane, and copolymers of urethane. The dilator hub 104 can be provided with an optional support tube (not shown) extending from its distal end and over a proximal section of the outer tube (not shown), to increase the rigidity of the deployment catheter during insertion. This support tube can be fabricated from any of a variety of materials, such as, for example, a stainless steel hypotube or a polymeric tube of high hardness such as, for example, polysulfone, polycarbonate, glass-filled polycarbonate, or the like. Alternatively, the two dilator tubes can be replaced by a single multi-lumen tube with one lumen capable of passing a guidewire therethrough and another lumen capable of inflating the balloon through skives or fenestrations placed through the tubing wall inside the balloon and operably connecting the balloon interior to the balloon inflation lumen. The distal end of the balloon inflation lumen of the multi-lumen tube is advantageously plugged or sealed 124 to prevent the escape of pressure from the balloon. The proximal end of the balloon inflation lumen is terminated and operably connected with the side port 108 of the dilator hub 104.

FIG. 2*a* illustrates the distal end of an embodiment of a radially expandable sheath 200 in its unexpanded configuration. The proximal end of the sheath 200 can be configured as described above. The sheath 200 comprises an expandable sheath tube 210 having a beveled distal end 212. The sheath further comprises a dilator central tube 202, a radiopaque marker 208, a balloon 206, a plurality of balloon bonds 218, and a tapered fairing 204. The tapered fairing 204 further comprises a fairing bond 216.

As shown in FIG. 2*a*, the radiopaque marker 208 is a generally cylindrical band or ring that is affixed around the outside of the dilator central tube 202 at or near its distal end. The distal end 212 of the beveled sheath tube 210 is cut at a slanted, or oblique, angle. The balloon 206 has a generally cylindrical structure with small diameter cylindrical ends which are affixed by the balloon bonds 218 to the central dilator tube 202. The tapered fairing 204 is affixed to the central dilator tube 202 by the fairing bond 216. In this embodiment, the tapered fairing 204 butts against, but does not overlap the beveled cut distal end 212 of the sheath tube 210. The tapered fairing 204 serves as a tissue dilator to ramp and deflect tissue radially outward as the sheath 200 is being advanced distally, thus preparing a channel in the tissue through which the sheath 200 is advanced. At least a portion of the angle subtended between the fairing tip 204 and the longitudinal axis of the sheath 200 can range between 1 degrees and 50 degrees and preferably between 2 and 10 degrees. The angle can vary along the length of the fairing tip 204. In this embodiment, the tapered fairing 204 substantially butts against or approaches, but does not overlap the perpendicularly cut distal end 214 of the sheath tube 210. The maximum diameter of the fairing 204, in the illustrated embodiment, is larger than the diameter of the expandable sheath distal tubing 210. In an embodiment, the maximum diameter of the fairing 204 is at least 10% larger than the maximum diametric dimension of the distal tubing 210. In an alternative embodiment, the maximum diameter of the fairing 204 can be substantially the same as the diameter of the distal tubing 210. The fairing 204 serves to deflect tissue radially outward so that it does not impinge or force itself into the interior lumen of the unexpanded distal sheath tubing 210 during insertion of the sheath 200.

FIG. 2b illustrates a partial breakaway view of the distal end of another embodiment radially expandable sheath 220 in its unexpanded configuration. The proximal end of the sheath 220 can be configured as described above. The distal end of the sheath 220 in this embodiment comprises an expandable sheath tube 222 having a perpendicularly cut distal end 224. The sheath 220 further comprises the dilator central tube 202, a tapered fairing 226, and the dilatation balloon 206. The dilation balloon further comprises the distal balloon bond 218, the radiopaque marker 208, and the fairing to tube bond 216.

As shown in FIG. 2b, the radiopaque marker 208 is a generally cylindrical band or ring that is affixed around the outside of the dilator central tube 202 at or near its distal end. The distal end 224 of the straight or perpendicularly cut sheath tube 222 is cut at right angles to the longitudinal axis of the tube 222. The balloon 206 is a generally cylindrical structure with small diameter cylindrical ends which are affixed by the balloon bonds 218 to the central dilator tube 202. The tapered fairing 226 is affixed to the central dilator tube 202 by the fairing bond 216. The radiopaque marker 208 is beneficially affixed to the dilator central tube 202 underneath the fairing to tube bond 216 to ensure complete entrapment of the radiopaque marker 208. In this embodiment, the tapered fairing 226 substantially butts against or approaches, but does not overlap the perpendicularly cut distal end 224 of the sheath tube 222. The maximum diameter of the fairing 226, in the illustrated embodiment, is larger than the diameter of the expandable sheath distal tubing 222. In an embodiment, the maximum diameter of the fairing 226 is at least 10% larger than the maximum diametric dimension of the distal tubing 222. In an alternative embodiment, the maximum diameter of the fairing 226 can be substantially the same as the diameter of the distal tubing 222. The fairing 226 serves to deflect tissue radially outward so that it does not impinge or force itself into the interior lumen of the unexpanded distal sheath tubing 222 during insertion of the sheath 220.

FIG. 3a illustrates the distal end of another embodiment of an expandable sheath system 300 in its unexpanded state. The proximal end of the sheath 300 can be configured as described above. The expandable sheath system 300 comprises a sheath 304 having a proximal non-expandable region 308, a transition zone 310 and a distal expandable region 312. The distal expandable region 210 further comprises a linear fold 314 and a straight cut distal end 316. The sheath system 300 further comprises the dilator tube 202, the radiopaque marker 208, and a tip fairing 324. The tip fairing 324 further comprises a proximal overlap region 326 and the fairing bond 216. The sheath system 300 further comprises the dilatation balloon 206 and the balloon bonds 218. The tip fairing 324 is shown in cross section while the dilator tube 202 and the radiopaque marker 208 are illustrated in a simple side view. The distal part of the expandable region 312 is shown in break away cross-sectional view.

As shown in FIG. 3a, the proximal non-expandable region 308 is affixed to the transition zone 310, which is affixed at its distal end to the distal expandable region 312. The central lumen of all three regions 308, 310, and 312 are operably connected. The dilator tube 202 is affixed to the dilatation balloon 206 with the plurality of balloon bonds 218. The tip fairing 324 is affixed to the dilator tube 202 by the fairing bond 216. A portion of the tip fairing 324 extends proximally to, or overlaps, the perpendicularly cut distal end 316 of the sheath tube distal end 312. The tip fairing 324 can tightly overlap the distal end 316 of the distal expandable region 312 or it can loosely shroud but not intimately contact the distal expandable region 312. The distal expandable region 312 and the transition region 310 both comprise the linear fold 314. The linear fold 314 is created by creasing the distal expandable region and a portion of the transition zone 310 longitudinally and forming a single, double, or triple crease, with a corresponding number of outward projections. The linear fold 314 permits the diameter or cross-section of the distal expandable region 312 to be reduced by one-third to three-fourths of diameter of the fully expanded configuration. The transition zone 310 is fully folded at its distal end to match the distal region 312 and is fully unfolded at its proximal end to match the configuration of the proximal, non-expandable region 308. The tip fairing 324 can be fabricated from materials such as, for example, Hytrel, polyester, silicone elastomer, thermoplastic elastomer, polyurethane, and the like. In an embodiment, materials suitable for use in the tip fairing 324 are advantageously elastomeric. These materials tend to possess higher friction than would materials such as PTFE, polyethylene, or the like. Therefore, the tip fairing 324 is advantageously coated with a lubricious material such as a hydrogel, hydrophilic coating, silicone oil, or the like, all with a low coefficient of sliding friction. The use of add-on material coatings such as Surgilube™ or other medical lubricious jelly is currently common but this coating can be rubbed off during insertion thus reducing its effectiveness. The above-listed coatings will not rub off or lose their effectiveness like the jelly. Under certain circumstances, it is beneficial as part of the manufacturing process to etch the surface of the fairing 324, using processes such as plasma discharge or chemical etching, prior to the coating step, to enhance the permanence of the coating.

FIG. 3b illustrates the distal end of the expandable sheath system 300 of FIG. 3a in its fully, radially expanded state. As set forth above, the expandable sheath system 300 comprises the proximal non-expandable region 308 and the distal expandable region 312 of the sheath 304. The distal expandable region 312 further comprises the straight cut distal end 316. The sheath system 300 further comprises the dilator tube 202, the dilatation balloon 206, and the tip fairing 324. The tip fairing 304 further comprises the proximal overlap region 326. The tip fairing 326 is shown in cross section while the dilator tube 202 and sheath 304 are shown in simple side view. A gap 334 is shown separating the fairing 304 from the distal end 214 of the sheath.

As shown in FIG. 3b, the proximal non-expandable region 308 is affixed to the transition zone 310, which is affixed at its distal end to the distal expandable region 312. The central lumen of all three regions 308, 310, and 312 are operably connected. The dilator tube 202 is affixed to the dilatation balloon 206 with a plurality of balloon bonds 218. The tip fairing 324 is affixed to the dilator tube 202 by the fairing bond 216. A portion of the tip fairing 324 can extend proximally to, or overlap, the perpendicularly cut distal end 316 of the sheath tube distal expandable region 312. However, due to the increase in diameter of the expanded balloon 206, the proximal end of the tip fairing 324 advantageously increases in diameter and is forced distally so as to no longer overlap or extend proximally to, the distal end 316 of the sheath tube expandable region 312, as illustrated. Thus, when the balloon 206 is deflated, the fairing 324 can be removed through the sheath 304.

FIG. 4a illustrates the distal region of another embodiment expandable sheath 400 comprising a proximal non-expandable region 402, a transition zone 404, and a distal expandable region 406. The proximal end of the sheath 400 can be arranged as described above. The distal expandable region 406 is terminated at its distal end by a straight or perpendicular cut 408. The expandable sheath 400 further comprises the dilator tube 202 and a distal fairing 410. The distal fairing further comprises a plurality of projections 416 and a plurality of intermediate gaps 418. The distal expandable region 406 further comprises an outer layer 420, a malleable reinforcing layer 422, and an inner layer 424.

As shown in FIG. 4a, the distal fairing 410 is configured at its proximal end with the plurality of proximally directed projections, fingers, tabs, or the like 416. The fingers 416 are integral, coupled or affixed, to the proximal end of the conically shaped or tapered distal fairing 410. The fingers 416 can be bonded or welded to the fairing 410 at or near its proximal end. One of the spacers or gaps 418 separates each pair of adjacent fingers 416. The gap 418 can have a width that approaches zero or it can have a width up to 500% that of the fingers 416. The distal fairing 410 is affixed to the dilator tube 202 by the fairing bond 216 (FIG. 2a). The axial length of the fingers 416 can range between 0.5 millimeter and 15 millimeters.

The distal expandable sheath region 406 possesses malleable characteristics that maintain their shape in the expanded or collapsed configuration. In the illustrated embodiment, the distal expandable sheath region 406 is rendered malleable by the reinforcing layer 422. In this embodiment, the reinforcing layer 422 comprises a coil of fully annealed stainless steel wire. The spacing between each turn of the coil can range from 0.001 inch to 0.5 inch. The thickness of the wire can range between 0.001 to 0.010 inch. The width of the wire can range from 0.003 to 0.050 inch. The stainless steel wire can be round, oval, trapezoidal, or rectangular in cross-section. The stainless steel wire used for the reinforcing layer 422 is preferably fully annealed by heat treating. The reinforcing layer 422 can also be fabricated from other malleable materials including, for example, tantalum, titanium, gold, platinum, cobalt nickel alloys, and the like. The reinforcing layer can also be in the form of a braid, weave, a stent, or the like. The reinforcing layer 422 can be sealed inside two polymeric layers, the outer layer 420 and the inner layer 424. The outer layer 420 can be welded or sealed to the inner layer 424 between the turns of the reinforcing layer 422. The outer layer 420 and the inner layer 424 can be fabricated from materials such as, for example, polyethylene, polypropylene, Hytrel, polyester, polyvinyl chloride, polyurethane, fluorinated polymers, or the like. The 406 has a structure such that when longitudinally folded, the reinforcing layer 422 retains its folded shape by overcoming any forces imparted by the polymeric outer layer 420 and the inner layer 424 and does not expand until forced to do so under control of the dilator balloon 206 (see FIGS. 3b and 4b). Once expanded, the expandable region 406 maintains its expanded shape by the strength of the reinforcing layer 422. The thickness of the expandable region can range from 0.005 inch to 0.040 inch. Other means of achieving dimensional stability without the need for a jacket or restraint include choosing polymeric materials that can take a set when creased. Further means of achieving malleability include heat setting the fold or crease in place on the tubing. Similar composite construction can be used for the proximal region 402 and the transition zone 404, although the materials used for the reinforcing layer 422 in the proximal non-expandable region 402 can advantageously be non-malleable with significant restorative capability.

FIG. 4b illustrates the distal end of the expandable sheath system 400 of FIG. 4a in its fully, radially expanded state. The expandable sheath system 400 comprises the proximal non-expandable region 408, the transition region 404, and the distal expandable region 406. The distal expandable region 406 comprises the straight cut distal end 408. The sheath system 400 further comprises the dilator tube 202, the dilator balloon 206, and the tip fairing 410. The tip fairing 410 comprises the plurality of fingers 416 and the plurality of circumferential gaps 418.

As shown in FIG. 4b, the proximal non-expandable region 402 is affixed to the transition zone 404, which is affixed at its distal end to the distal expandable region 406. The central lumen of all three regions 402, 404, and 406 are operably connected. The dilator tube 202 is affixed to the dilatation balloon 206 with the plurality of balloon bonds 218 (FIG. 2a). The tip fairing 410 is affixed to the dilator tube 202 by the fairing bond 216 (FIG. 2a). A portion of the tip fairing 410 is configured with proximally directed projections, which extend proximally to, or overlap, the perpendicularly cut distal end 408 of the sheath tube distal expandable region 406. However, due to the increase in diameter of the expanded balloon 206, the proximal end of the fingers or projections 416 of the tip fairing 410 advantageously increase in diameter and are forced distally so as to no longer overlap or extend proximally to the distal end 408 of the sheath tube expandable region 406, as illustrated.

FIG. 5a illustrates the distal region of an expandable sheath 500 similar to the sheath 400 of FIGS. 4a and 4b, and like elements are numbered accordingly. In particular, the sheath 500 includes the proximal non-expandable region 402 affixed to the transition zone 404, which is affixed at its distal end to the distal expandable region 406. The central lumens of all three regions 402, 404, and 406 are operably connected to each other. The sheath 500 further includes the dilator tube 202, the dilator balloon 206 and the fairing 410 described above. The fairing 410 includes the plurality of proximally directed projections, fingers, tabs, or the like 416. The fingers 416 are integral, or affixed, to the proximal end of the conically shaped or tapered distal fairing 410. One of the spacers or gaps 418 separates each pair of adjacent fingers 416. The sheath 500 further comprises a secondary fairing 502 which comprises secondary fairing projections or fingers 504. The secondary fairing 502 is affixed to the tapered distal fairing 410 by a fairing to fairing bond 510. The fingers or projections 502 of the secondary fairing 502 are configured to overlap the gaps 418 between the fingers or projections 416 of the primary fairing 410. In FIG. 5a, the sheath 500 is shown in its unexpanded configuration. The dilatation balloon 206 is partially expanded and is visible in this partial cutaway view.

FIG. 5b illustrates a side view of the sheath 500 of FIG. 5a in its expanded, radially dilated configuration. As shown in FIGS. 5a and 5b, the primary distal fairing 410 is affixed to the secondary distal fairing 502 by the fairing to fairing bond 510. The fairing to fairing bond 510 can extend substantially the entire length of the fairings 502 and 410 but beneficially does not extend into the region where the fingers 416 and 504 reside, thus permitting the fingers 416 and 504 to move separately and not as a unit structure. The fairing to faring bond 510 can be in the form of a heat weld, adhesive bond, solvent bond, ultrasonic weld, mechanical interlock, or any other suitable fixation methodology. In FIG. 5a, the transition zone 404 and the distal region 406 have dilated to substantially the same size as the proximal region 308. Accordingly, the separations between the three zones are shown as dashed lines. The fingers 416 of the primary tapered fairing 410 and the fingers 504 of the secondary tapered fairing 502 have retracted distally so as to substantially uncover the distal end of the distal region 406. In the illustrated embodiment, the proximally projecting fingers 416 and 504, respectively, take on a trapezoidal shape, which differs from their original roughly rectangular shape since they are stretched circumferentially at their attachment points to the primary tapered fairing 410 and the secondary tapered fairing 502 but are substantially un-stretched at their free (proximal) ends. The fingers 416 and 504, respectively, can be integral to, bonded to, welded to, or otherwise affixed to the primary tapered fairing 410 and the secondary tapered fairing 502. The primary fairing 410 and the secondary fairing 502 can be fabricated from materials such as, for example, Hytrel, polyester, silicone elastomer, thermoplastic elastomer, polyurethane, or other suitable polymer. The materials of the primary fairing 410 and the secondary fairing 502 need not be the same but they are beneficially able to be affixed to one another and to the dilator shaft 202. The materials of the primary fairing 410 and 502 can further comprise bismuth or barium salts, tantalum, gold, platinum, or other radio-dense materials to maximize the radiopacity of the fairings 410 and 502 so that they are optimally visible under fluoroscopy. The concentration of radiopaque materials should not exceed 50% of the total mass in order to sustain an acceptable structural integrity.

Figures 6A, 6B:
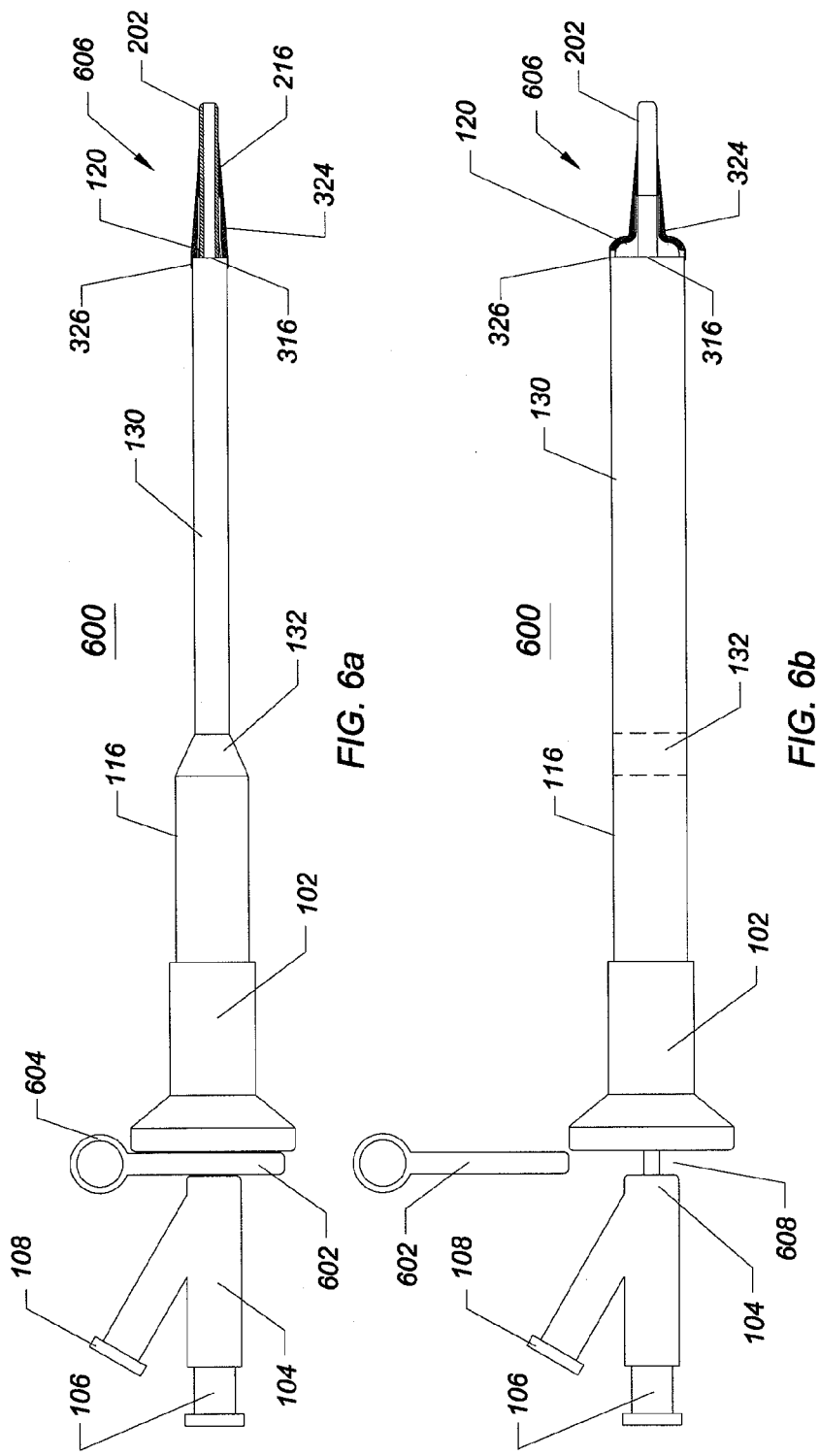
FIG. 6a is a side, partial cutaway, view of an unexpanded medical access sheath comprising a stop at the proximal end of the sheath to limit relative axial motion between the sheath and the dilator, according to an embodiment of the invention.
FIG. 6b is a side, partial cutaway, view of the medical access sheath in its radially expanded configuration with the stop at the proximal end of the sheath having been removed, according to an embodiment of the invention.

FIG. 6a illustrates a medical access sheath 600 similar to the sheath 100 of FIGS. 1a and 1b, and like elements are numbered accordingly. In particular, the sheath 600 comprises the proximal sheath tube 116, the transition zone 132 and the distal expandable sheath tube 130. The sheath 600 further comprises the sheath hub 102, the dilator hub 104 and the balloon 120 of FIGS. 1a and 1b, the dilator tube 202 of FIGS. 2a and 2b, and the tip fairing 324 of FIGS. 3a and 3b. The dilator hub 104 further comprises the balloon inflation port 108 and the guidewire port 106. The tip fairing 324 further comprises the overlap region 326 and the fairing to tube bond 216. As shown in cross section, the tip fairing 324 is positioned against the straight-cut distal end 316 of the expandable sheath tube 130 with the overlap region 326 extending a short distance along the sheath tube 130. In FIG. 6a, the dilator 606 (e.g., the distal end portion of the sheath 600) is illustrated in its radially or diametrically collapsed configuration. The sheath 600 further comprises a removable stop or hub interlock 602, which comprises a handle 604.

As shown in FIG. 6a the hub interlock 602, which can also be referred to as a stop, is inserted between the sheath hub 102 and the dilator hub 104. A slot (not shown) in the hub interlock 602 allows the hub interlock 602 to be inserted over the dilator tube 202. In this configuration, the sheath 600 can be inserted into the patient with assurance that the dilator hub 104 cannot move distally relative to the sheath hub 102. Thus, the overlap region 326 of the fairing 324 cannot move distally relative to the distal end 314 of the dilator expandable region 130 and no exposed gap is formed between the fairing 324 and the sheath expandable region 130.

FIG. 6b illustrates the medical access sheath 600 of FIG. 6a in its radially expanded configuration and further illustrates the sheath interlock 602 removed, thus exposing a gap 608 between the dilator hub 104 and the sheath hub 102. With the distal end of the sheath 130 radially dilated to substantially its maximum level, the transition zone 132, shown in FIG. 6a, is no longer visible. The distal end of the dilator 606 is shown in a partial breakaway view with the fairing 324 shown in cross-section but with the balloon 120 and the dilator tube 202 shown in simple exterior view. Since the balloon 120 is transparent and the fairing 324 is shown in cross-section, the dilator tube 202 is completely visible where it extends distally of the distal edge 316 of the distal sheath tubing 130. The overlap portion 326 remains slightly proximal of the distal edge 326 in this embodiment, even after expansion of the balloon 120.

FIG. 7a illustrates a side view of an expandable medical sheath 700 comprising elements shown in FIGS. 6a and 6b, which are numbered accordingly. The sheath system 700 further includes a plurality of packaging clips 702 removably affixed to the distal expandable region 130 to protect the cross-sectional configuration of the unexpanded sheath during shipment and storage. Two packaging clips 702 are illustrated in FIG. 7a. Each of the packaging clips 702 comprises an optional grip tab 704 and a sleeve 706. The sleeve 706 has a C-shaped cross-sectional profile. The packaging clips 702 are applied to the distal region 130 at locations distal to the transition zone 132. Preferably, the packaging clips 702 are located so that they extend substantially proximate the distal end and the proximal end of the expandable region 130. In another embodiment, a single packaging clip 702 is applied, rather than a plurality of packaging clips 702. In the single packaging clip 702 embodiment, the packaging clip 702 can be longer and extend substantially along the complete length of the distal expandable region 130. The packaging clips 702 can be fabricated from polymeric materials, metals, or ceramics. Suitable polymeric materials include, for example, polyethylene, polypropylene, polytetrafluoroethylene, polyamide, polyimide, polycarbonate, polyester, and the like. Suitable metals include, for example, stainless steel, cobalt nickel alloy, titanium, nitinol, and the like. The packaging clip 702 is preferably fabricated so that it is large and obviously needs to be removed prior to introduction into the patient. The packaging clip 702 can comprise the optional grip tab 704 or other handle to facilitate removal. The packaging clip 702 can comprise embossed lettering, raised lettering, or printed lettering with indications to remove prior to use.

FIG. 7b illustrates a side view of the expandable medical access sheath 700 of FIG. 7a wherein the clips 702 have been removed. In the illustrated embodiment, the clips 702 have been removed from a lateral or radial direction and not by sliding them distally along the longitudinal axis of the sheath distal region 130. In the illustrated embodiment, the distal clip 702 remains in its original orientation while the proximal clip 702 has been rotated 90 degrees to show its cross-sectional profile. The C-shape is configured to extend around more than 180 degrees of the circumference of the generally cylindrical cross-section to prevent inadvertent removal of the clip 702 from the sheath distal region 130. The wall thickness of the clip 702 is chosen to permit flexibility so that the clip 702 can expand radially for application without deforming the sheath distal region 130. The relaxed inner diameter of the clip 702 is chosen to approximate the desired outside diameter of the distal region 130 in its collapsed configuration.

FIG. 8a illustrates the sheath 600 of FIGS. 6a and 6b with the sheath expandable region 130 having been radially expanded and the balloon 120 of the dilator 606 having been deflated or re-collapsed. In this illustration, the dilator 606 has been advanced distally as far as possible to close the gap 608 between the sheath hub 102 and the dilator hub 104. The fairing 324 with its overlap region 326 moves distally a corresponding amount relative to the distal edge 316 of the sheath distal, expandable region 130. In this embodiment, the overlap region 326 of the fairing 324 has completely cleared the distal edge 316 of the distal sheath tubing 130 and has elastically recoiled to a diameter smaller than that of the lumen (not shown) of the sheath tubing 130. The dilator 606 can now be withdrawn proximally from the sheath tubing 130 and 116 and the sheath hub 102.

FIG. 8b illustrates a side view of the medical access sheath 600 of FIGS. 6a, 6b, and 8a wherein the dilator 606 is being withdrawn proximally through the sheath tubing 116 and 130 in preparation for removal. The dilator hub 104 is moving proximally away from the sheath hub 102. The tapered fairing 324 and its overlap region 326 have cleared the distal edge 316 of the sheath tubing 130 and loosely slide within the lumen of the sheath tubing 130 and 116. The balloon 120 is fully collapsed and also fits through the sheath tubing 130 and 118. In this illustration, the tapered fairing 324 is shown in cross-section and the distal end of the expandable sheath tubing 130 is shown in breakaway cross-sectional view.

FIG. 9a illustrates a side view of another embodiment unexpanded medical access sheath 900 comprising an unexpandable proximal portion 902, a transition portion 904 and an expandable portion 906. The expandable portion includes a distal edge 910, which is bevel cut at an angle in a range of 20 to 70 degrees from the longitudinal axis of the sheath 900. The expandable portion 906 and at least a portion of the transition portion 904 include folds 912, which reduce the cross-sectional area as described above. The sheath 900 includes the dilator tube 202 and the balloon 206 (shown in FIG. 9b). The sheath 900 further comprises a distal fairing 922 that includes a longitudinal slit 924 along at least a portion of the length of the distal fairing 924. The longitudinal slit 924 further comprises an optional strain relief 926 at one or both ends of the longitudinal slit 924 to prevent tearing of the distal fairing 922. The distal fairing 922 is affixed to the dilator tube 202 by the fairing bond 216. The distal fairing 902 does not overlap the distal expandable region 210 of the sheath 900.

FIG. 9b illustrates the sheath 900 of FIG. 9a wherein the sheath 900 has been expanded by the dilator (e.g., the balloon 206). The distal fairing 922 has expanded at its proximal edge and the longitudinal slit 924 has opened to facilitate retraction of the proximal edge of the distal fairing 922. The distal fairing 922 has pulled away from the distal edge 910 of the sheath expandable region 906 and the longitudinal fold 908 (FIG. 9a) has unfolded and so no longer is present in FIG. 9b. The dilator tube 202 is visible through the expanded longitudinal slit 924 and the transparent balloon 206.

FIG. 10a is a side view of another embodiment of the expandable sheath 1000 similar to the sheath 100 in FIGS. 1a and 1b. In FIG. 10a, a portion of the sheath hub 102 wall is broken away to view interior components of the dilator hub 104 and to show an intermediate dilator tube 1008. A portion of the distal outermost portion of the dilator hub 104 has also been broken away to reveal an outer support collar 1016 in cross-section, an engagement tab 1004, and an inner support collar 1014. The dilator hub 104 comprises the inflation port 108, the guidewire port 106, and can comprise at least one engagement tab 1004 and a hub grip 1002. The sheath hub 102 is a soft hub formed from and integral to the proximal sheath tubing 116. The sheath hub 102 can comprise an engagement slot 1006 (FIG. 10b). The sheath system 1000 comprises the proximal non-expandable tubing 116, the transition zone 132, and the distal expandable tubing 130. The sheath 1000 comprises a dilator 1026 further comprising the inner dilator tube 202. The sheath 1000 also comprises a distal fairing 1030 further comprising a loose overlap region 1032, which is illustrated more clearly in FIG. 10c in an enlarged partial cross-sectional view of the distal edge of the access sheath and the proximal portion of the tapered fairing bounded by the circle in FIG. 10a.

In an embodiment, the dilator hub 104 is keyed so that when it is interfaced to, or attached to, the sheath hub 102, the two hubs 104 and 102 cannot rotate relative to each other. This is beneficial so that the balloon 120 or the dilator inner tubing 202 does not become twisted due to inadvertent rotation of the dilator hub 104 relative to the sheath hub 102. A twisted balloon 120 has the potential of not dilating fully because the twist holds the balloon 120 tightly to the dilator inner tubing 202 and prevents fluid from fully filling the interior of the balloon 120. Twisting of the dilator inner tubing 202 or the balloon 120 has the potential for restricting guidewire movement within the guidewire lumen 118 (not shown) or adversely affecting inflation/deflation characteristics of the balloon 120. Thus, the anti-rotation feature of the two hubs 104 and 102 is beneficial. In certain embodiments, the anti-rotation features can include mechanisms or means such as, for example, one or more keyed tab (not shown) on the sheath hub 102 and one or more corresponding keyed slot (not shown) in the dilator hub 104. Axial separation motion between the dilator hub 104 and the sheath hub 102 disengages the two hubs 104 and 102 while rotational relative motion is prevented by the sidewalls of the tabs 1004 and the slots 1006. The number of tabs 1004 and slots 1006 can range from 1 to as many as 10 or more. A draft angle on the sidewalls of the tabs 1004 and the slots 1006 further promotes engagement and disengagement of the anti-rotation feature. In another embodiment, the sheath hub 102 is releasably affixed to the dilator hub 104 so the two hubs 102 and 104 are coaxially aligned and prevented from becoming inadvertently disengaged or separated laterally. In this embodiment, the dilator hub 104 and the sheath hub 102 are connected at a minimum of 3 points, which prevent lateral relative motion in both of two substantially orthogonal axes. In a preferred embodiment, the two hubs 102 and 104 are engaged substantially around their full 360-degree perimeter. Manual pressure is sufficient to snap or connect the two hubs 102 and 104 together as well as to separate the two hubs 102 and 104. The slot 1006 (FIG. 10b) can be a cut completely through the wall of the hub 102, it can be partially cut into the hub 102 wall, or it can be formed from a radially inwardly projecting wall on the hub 102.

The distal fairing 1030 is configured to taper smoothly to the diameter of the inner tubing 202 at its distal end and to a diameter larger than that of the collapsed, expandable sheath tubing 130 such that the overlap region 1032 loosely covers the distal edge of the expandable sheath tubing 130 for the purpose of preventing tissue from impinging on the distal edge of the sheath tubing 130 when advanced into the body in its collapsed, unexpanded state. Once expanded, the overlap region 1032 and the distal fairing 1030 are elastically expanded and exert a restorative force against the balloon 120. The overlap region 1032 can exert a restorative radially directed inward force against the sheath tubing 130 unless the overlap region 1032 has retracted distally off of the overlap region 1032.

FIG. 10b illustrates a side view of an expandable medical sheath 1000 comprising the dilator assembly 1026. The sheath assembly 1000 is shown with a breakaway view of the distal end to reveal the dilator assembly 1026 within, which is shown in cross-section. The sheath assembly 1000 further comprises a sheath hub 102, and the dilator assembly 1026 further comprises a dilator hub 104. The dilator hub 104 comprises the anti-rotation tab or pin 1004, the optional outer support collar 1016, and the inner support collar 1014 (FIG. 10a). The sheath hub 102 further comprises the anti-rotation slot 1006. The sheath assembly 1000 further comprises the sheath tubing 116 and 130 while the dilator assembly 1026 further comprises the inner dilator shaft 202, the dilator balloon 120, the intermediate tube 1008 and the guidewire lumen 118. The space between the intermediate tube 1008 and the inner tube 202 forms an annulus 1010 that operably connects the interior of the balloon 120 with the balloon inflation port 108.

As shown in FIG. 10b, the sheath hub 102 can be a separate polymeric or metallic component, which is bonded to, or mechanically affixed to, the proximal sheath tubing 116. The sheath hub 102, in a preferred embodiment, can be a diametric enlargement on the proximal end of the proximal sheath tubing 116 and can further be integral to the sheath tubing 116. The sheath tubing 116 and 130 preferably is capable of remolding or deforming to become elliptical or oval. In an embodiment, the sheath hub 102 is also capable of deforming or remolding with the proximal sheath tubing 116. In an embodiment, the dilator hub 104, which comprises the anti-rotation pin or protrusion 1004, an optional outer support collar (not shown), and an inner support collar 1014, comprises all three elements integrally formed to each other or bonded to each other. The integral forming can be done by machining, injection molding, thermoforming, or the like. The guidewire lumen 118 is an interior through lumen, which is preferably concentrically disposed at the center of the dilator inner shaft 202, although it may also be an off-center through lumen.

Both the inner tube 202 and the guide wire lumen 118 extend through the distal end of the balloon 120. The inner tube 202 can carry coaxially, on its exterior or embedded within the tubing wall, a proximal marker ring 1040, a distal marker ring 1042, or both, near the proximal end and the distal end of the balloon 120, respectively. The markers 1040 and 1042 can be fabricated from materials such as, for example, gold, tantalum, platinum or another radiopaque material suitable for visualization under fluoroscopy. The markers 1040 and 1042 can be configured as rings, solids, spirals, wire formations, or other suitable structure. Additional radiopaque markers can be affixed to the expandable sheath tubing 130 or to the dilator 1026 to aid in visualizing its location.

As shown in FIG. 10*b*, a balloon inflation lumen or annulus 1010, defined in the space between the inner tube 202 and the intermediate tube 1008, communicates with the interior of the balloon 120. As discussed above, the balloon 120 can be inflated to expand the distal section 130 of the medical access sheath 1000 from its first, smaller cross-sectional profile to its second, larger cross-sectional profile. Thus, the length of the balloon 120 is approximately equal to or slightly longer than the length of the distal section 130. In the illustrated embodiment, which is configured for percutaneous nephrostomy, the length of the balloon 120 is in a range from approximately 10 centimeters to approximately 30 centimeters. For other clinical applications, the length of the balloon 120 can be in the range from about 4 centimeters to about 90 centimeters. The proximal balloon bond 1012 affixes the balloon 120 at its proximal end to the intermediate tubing 1008 and provides a fluid tight seal to prevent the escape of fluid either into or out of the interior of the balloon 120.

The inner tube 202 and the guidewire lumen 118 both extend through to substantially the distal end of the Y-connector or dilator hub 104. The Y-connector 104 advantageously comprises the guidewire hole, port or lumen 106 that operably connects to the guidewire lumen 118 to permit complete through passage of the guidewire or other material. The balloon inflation annulus 1010, defined in the space between the inner tube 202 and the intermediate tube 1008, opens into the inflation port 108 in the Y-connector or dilator hub 104. Only the inflation port 108 operably communicates via the balloon inflation lumen or annulus 1010 with the interior of the balloon 120. A pump (e.g., a syringe pump) may be connected to the inflation port 108 to inflate or deflate the balloon 120. In a modified embodiment, an inflation device or pump (e.g., a syringe pump) may be pre-attached or integrally formed with the port 108. The inflation device (not shown) may be pre-loaded with inflation material. To enable visualization of the state of the balloon 120, the balloon may be inflated with contrast media. Suitable inflation materials include, but are not limited to, saline, water, gas, contrast media such as Renografin® or Omnipaque®, or the like. The inflation material is preferably sterile to minimize the risk of infection should a fluid leak occur.

The balloon 120 can be fully inflated to expand the distal section 130 of the medical access sheath to its full cross-sectional profile. The cross-sectional profile of the distal section 130 can be round, it can be approximately oval, or it can be configured with any type of irregular profile. In one embodiment, the balloon 120 can be inflated by providing a pump (e.g., a high pressure balloon inflation syringe) with about 20-25 cc or more of a diluted contrast media (e.g., a 50% solution of Renografin® and sterile saline). After removing the air from the pump and associated tubing, the pump may be attached to the inflation/deflation port of the central balloon shaft. Preferably, under fluoroscopic control, the dilute contrast media is slowly injected until a maximum pressure of about 12 to 25 bar is achieved. Inflation pressure is preferably maintained for a minimum of about 15 to 60 seconds to reduce or eliminate any "waists" (i.e., partially unexpanded sections) that may remain along the length of the expanded sheath 1000.

As shown in FIGS. 10*a*, 10*b*, 8*a*, and 8*b*, after the balloon 120 is inflated, it may be deflated to ease the removal of the dilator or deployment catheter 606. As discussed above, the inflation and deflation of the balloon 120 can be accomplished via a pump connected to the port 108 of the dilator hub 104. Preferably, a dilute radiopaque contrast media is pumped into the balloon 120, to better convey the state of the balloon 120 to an observer by way of fluoroscopic imaging. As shown in FIGS. 8*a* and 8*b*, following deflation of the balloon 120, the tapered fairing 1030, elastically recoils to its smaller, original diameter. The proximal region 1032 of the tapered fairing 1030, which loosely overlaps the distal edge of the sheath tubing 130 when unexpanded, collapses to a diameter smaller than that of the expanded distal sheath tubing 130. The radial collapse of the tapered fairing 1030 permits proximal, or retrograde, removal of the dilator assembly 1026 from the interior lumen of the sheath tubing 130 and 116.

With the deployment catheter or dilator 1026 removed, the medical access sheath 1000 can extend into the renal pelvis and provide a working lumen for instrumentation or inspection. The establishment of this working lumen may provide access for several procedures such as biopsy, stone extraction, antegrade endopyelotomy, and resection of transitional cell carcinoma of the upper urinary tract. As shown in FIG. 2*a*, in the embodiments with a beveled edge 212, the leading edge maintains positional purchase within the target tissue or organ while the trailing edge provides the sheath 1000 with an aperture to facilitate instrument maneuvering and visualization within the internal structure of the tissue or organ under examination or repair.

It will be apparent from the disclosure herein that the medical access assemblies, and/or the methods described herein may also find utility in a wide variety of diagnostic or therapeutic procedures that require an artificially created or natural access tract. For example, the embodiments described herein may be used in many urological applications (e.g., the removal of ureteral strictures and stones, the delivery of drugs, RF devices and radiation for cancer treatment, etc.). In such applications, the medical access sheath 1000 may have a length of about 30-300 centimeters with an unexpanded diameter of about 7-20 French and an expanded diameter of about 14-60 French. The sheath 1000 may also be used in many gastrointestinal applications, which require the introduction of a surgical retractor (e.g., to the removal gallstones and appendix procedures). In such applications, the medical access sheath 1000 may have a length of about 10 centimeters to about 50 centimeters with an unexpanded diameter of about 3-15 French and an expanded diameter of about 15-60 French. The medical access sheath 1000 may also be used as an access catheter for many gastrointestinal applications (e.g., colon therapies, esophageal treatment and the treatment of bowel obstructions). In such applications, the medical access sheath 1000 may have a length of about 30-300 centimeters with an unexpanded diameter of about 7-40 French and an expanded diameter of about 14-120 French.

The sheath 1000 is suitable for use on any suitable biological body, such as that of a mammal or reptile. The sheath can be beneficially used on human patients and is especially suited to percutaneous access for therapeutic or diagnostic purposes. The sheath may also be used in many cardiovascular applications (e.g., to provide access for minimally invasive heart bypass, valve replacement or the delivery of drugs or angiogenesis agents). In such applications, the medical access sheath 1000 may have a length of about 30-300 centimeters with an unexpanded diameter of about 3-12 French and an expanded diameter of about 5-30 French. For vascular applications (e.g., minimally invasive access to the aorta or contralateral leg arteries for the treatment of, for example, an abdominal aortic aneurysm), the medical access sheath 1000 may have a length of about 30-300 centimeters with an unexpanded diameter of about 5-30 French and an expanded diameter of about 15-75 French. For gynecological applications (e.g., endometrial therapies, delivery of drugs, delivery of cancer agents, sterilization procedures, etc.), the medical access sheath 1000 may have a length of about 10-100 centimeters with an unexpanded diameter of about 3 French to 20 French and an expanded diameter of about 6 French to 60 French. The cardiovascular access embodiment of the expandable sheath comprises valves and seals, such as hemostasis valves, stopcocks, Tuohy-Borst valves, and the like, at the proximal end to prevent blood loss or the ingress of air into the cardiovascular system.

In the embodiment of FIG. 4a, the reinforcing layer 412 can further comprise one or more longitudinally oriented elements 416. These longitudinally disposed elements 416 can be used to provide additional column strength to the composite structure. A single longitudinal element can provide significantly enhanced column strength while maintaining lateral flexibility, a desirable feature when inserting a catheter, introducer, or sheath into the body.

Although the invention has been described in terms of certain preferred embodiments, other embodiments of the invention including variations in dimensions, configuration and materials will be apparent to those of skill in the art in view of the disclosure herein. In addition, all features discussed in connection with anyone embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A medical access system adapted for providing minimally invasive access to a biological body, comprising:
an access sheath comprising an axially elongate tubular body that defines a lumen, at least a distal portion of the elongate tubular body being expandable from a first, folded, smaller cross-sectional profile to a second, greater cross-sectional profile to form an expanded distal portion of the sheath, the access sheath having a distal edge;
a dilator slidably disposed within the lumen of the axially elongate tubular body, wherein the dilator has a first, non-expanded configuration and has a second, expanded configuration, which is capable of expanding the first, folded smaller, cross-sectional profile of the access sheath into the second, greater cross-sectional profile of the access sheath; and
a tapered distal fairing that shields the distal edge of the access sheath from tissue as the sheath is being advanced distally into the body, wherein the distal fairing is affixed to the dilator, and a proximal end of the tapered distal fairing has an inside diameter that expands to approximately the same diameter as the outside diameter of the dilator when the dilator is in its expanded configuration and has an outside diameter that contracts to a diameter smaller than an inside diameter of the expanded distal portion of the access sheath when the dilator collapses to a collapsed configuration;
wherein the proximal end of the tapered distal fairing overlaps the distal edge of the axially elongate tubular body without any radially directed inward force when the axially elongate tubular body is in its first, non-expanded configuration.

2. The medical access system of claim 1, wherein the tapered distal fairing can be withdrawn proximally following expansion and subsequent re-collapse of the dilator.

3. The medical access system of claim 1 wherein the proximal edge of the tapered distal fairing comprises proximally directed projections separated by a space equal to at least 10% of the circumferential width of the projections.

4. The medical access system of claim 1 wherein the proximal edge of the tapered distal fairing comprises a first layer and a second layer of proximally directed projections, wherein the first layer is circumferentially offset from the second layer such that the proximally directed projections substantially overlap each other.

5. The medical access system of claim 1, wherein the proximal edge of the tapered distal fairing comprises a first layer of proximally directed projections and a second layer of proximally directed projections wherein the first layer of proximally directed projections is affixed to the second layer of proximally directed projections at a location distal to a distal extent of the first and second layer of projections.

6. The medical access system of claim 1, wherein the tapered distal fairing comprises elastomeric polymer.

7. The medical access system of claim 1, wherein the sheath is adapted for use in percutaneous procedures.

8. The medical access system of claim 1, wherein the sheath is adapted for use in transluminal procedures.

9. The medical access system of claim 1, wherein the sheath is adapted for use in performing percutaneous nephrolithotomy.

10. The medical access system of claim 1, wherein the sheath is adapted for use in performing ureteroscopy.

11. The medical access system of claim 1, wherein the sheath is adapted for use in performing urological procedures.

12. The medical access sheath system of claim 1, wherein the axially elongate tubular structure is terminated with an edge that is substantially perpendicular to the axis of the axially elongate tubular structure.

13. The medical access sheath system of claim 1, wherein the axially elongate tubular structure is terminated with an edge that is cut at an oblique angle relative to the longitudinal axis of the axially elongate tubular structure.

14. The medical access sheath system of claim 1, further comprising a packaging clip, wherein the packaging clip is removed from the sheath system prior to introduction of the system in a patient.

15. The medical access sheath system of claim 1, further comprising a plurality of packaging clips, wherein the packaging clips are removed from the sheath system prior to introduction of the system in a patient.

16. The medical access sheath system of claim 1, further comprising a packaging clip, wherein the packaging clip comprises a "C-shaped" cross-section which permits removal of the clip in a lateral direction.

17. The medical access sheath system of claim 1, wherein the axial slidability of the dilator relative to the sheath can be selectively arrested or enabled by a user controllable lock.

18. The medical access sheath system of claim 1, wherein the expansion from the first, folded smaller, cross-sectional profile into the second, greater cross-sectional profile is generated by radial expansion of the dilator while locked in an axial position.

19. The medical access sheath system of claim 1 further comprising a guidewire lumen within the dilator.

20. The medical access sheath system of claim 1 wherein the sheath and dilator do not comprise a guidewire lumen.

21. A medical access system adapted for providing minimally invasive access to a biological body, comprising:
   an access sheath comprising an axially elongate tubular body that defines a lumen, at least a distal portion of the elongate tubular body being expandable from a first, folded, smaller cross-sectional profile to a second, greater cross-sectional profile to form an expanded distal portion of the sheath, the access sheath having a distal edge;
   a dilator slidably disposed within the lumen of the axially elongate tubular body, wherein the dilator has a first, non-expanded configuration and has a second, expanded configuration, which is capable of expanding the first, folded smaller, cross-sectional profile of the access sheath into the second, greater cross-sectional profile of the access sheath; and
   a tapered distal fairing that shields the distal edge of the access sheath from tissue as the sheath is being advanced distally into the body, wherein the distal fairing is affixed to the dilator, and a proximal end of the tapered distal fairing has an inside diameter that expands to approximately the same diameter as the outside diameter of the dilator when the dilator is in its expanded configuration and has an outside diameter that contracts to a diameter smaller than an inside diameter of the expanded distal portion of the access sheath when the dilator collapses to a collapsed configuration;
   wherein the proximal edge of the tapered distal fairing comprises proximally directed projections with discontinuities or slits between the projections.

22. A medical access system adapted for providing minimally invasive access to a biological body, comprising:
   an access sheath comprising an axially elongate tubular body that defines a lumen, at least a distal portion of the elongate tubular body being expandable from a first, folded, smaller cross-sectional profile to a second, greater cross-sectional profile to form an expanded distal portion of the sheath, the access sheath having a distal edge;
   a dilator slidably disposed within the lumen of the axially elongate tubular body, wherein the dilator has a first, non-expanded configuration and has a second, expanded configuration, which is capable of expanding the first, folded smaller, cross-sectional profile of the access sheath into the second, greater cross-sectional profile of the access sheath; and
   a tapered distal fairing that shields the distal edge of the access sheath from tissue as the sheath is being advanced distally into the body, wherein the distal fairing is affixed to the dilator, and a proximal end of the tapered distal fairing has an inside diameter that expands to approximately the same diameter as the outside diameter of the dilator when the dilator is in its expanded configuration and has an outside diameter that contracts to a diameter smaller than an inside diameter of the expanded distal portion of the access sheath when the dilator collapses to a collapsed configuration;
   wherein the distal tapered fairing is coated with a lubricious material that is resistant to being wiped off.

23. The medical access system of claim 22, wherein the proximal end of the tapered distal fairing butts up against but does not overlap the distal edge of the axially elongate tubular body.

24. The medical access system of claim 22 wherein the proximal end of the tapered distal fairing overlaps the distal edge of the axially elongate tubular body.

* * * * *